United States Patent
Do

(10) Patent No.: US 9,206,457 B2
(45) Date of Patent: Dec. 8, 2015

(54) UTILIZATION OF PHARMACOLOGICAL CHAPERONES TO IMPROVE MANUFACTURING AND PURIFICATION OF BIOLOGICS

(75) Inventor: Hung V. Do, New Hope, PA (US)

(73) Assignee: Amicus Therapeutics, Inc., Cranbury, NJ (US)

( * ) Notice: Subject to any disclaimer, the term of this patent is extended or adjusted under 35 U.S.C. 154(b) by 0 days.

(21) Appl. No.: 12/952,036

(22) Filed: Nov. 22, 2010

(65) Prior Publication Data

US 2011/0143419 A1     Jun. 16, 2011

Related U.S. Application Data

(63) Continuation-in-part of application No. 12/788,068, filed on May 26, 2010, now abandoned.

(60) Provisional application No. 61/181,255, filed on May 26, 2009.

(51) Int. Cl.

| | |
|---|---|
| *C12P 21/02* | (2006.01) |
| *C07D 201/00* | (2006.01) |
| *C12N 5/07* | (2010.01) |
| *C12N 5/10* | (2006.01) |
| *C12N 9/00* | (2006.01) |
| *C07K 5/00* | (2006.01) |
| *C07K 7/00* | (2006.01) |
| *C07K 16/00* | (2006.01) |
| *C07K 17/00* | (2006.01) |
| *A61K 38/00* | (2006.01) |
| *C07K 1/14* | (2006.01) |
| *C07K 1/22* | (2006.01) |

(52) U.S. Cl.
CPC .............. *C12P 21/02* (2013.01); *C07D 201/00* (2013.01); *C07K 1/14* (2013.01); *C07K 1/22* (2013.01); *C12Y 302/01054* (2013.01)

(58) Field of Classification Search
None
See application file for complete search history.

(56) References Cited

U.S. PATENT DOCUMENTS

| | | |
|---|---|---|
| 2005/0203019 A1 | 9/2005 | Conn |
| 2007/0021381 A1 | 1/2007 | Fan et al. |
| 2007/0178081 A1* | 8/2007 | Fan ............................ 424/94.61 |
| 2008/0009516 A1 | 1/2008 | Wustman |
| 2010/0197018 A1 | 8/2010 | Mugrage |
| 2010/0330617 A1* | 12/2010 | Reczek et al. ............... 435/69.1 |

FOREIGN PATENT DOCUMENTS

| | | |
|---|---|---|
| WO | WO-2004/074450 | 9/2004 |
| WO | WO-2008/054947 | 5/2008 |

OTHER PUBLICATIONS

Graaf et al., Cloning and characterization of human liver cytosolic b-glycosidase, Biochem. J. (2001) 356, 907-910 (Printed in Great Britain).*

(Continued)

*Primary Examiner* — Reza Ghafoorian
(74) *Attorney, Agent, or Firm* — Servilla Whitney LLC

(57) ABSTRACT

The present invention provides methods for improving the production of recombinant proteins through the use of pharmacological chaperones for the recombinant proteins. As exemplified by the present invention, the binding of a pharmacological chaperone to a recombinant protein expressed by a cell can stabilize the protein and increase export of the protein out of the cell's endoplasmic reticulum, and increase secretion of the protein by the cell.

7 Claims, 17 Drawing Sheets

(56) References Cited

OTHER PUBLICATIONS

Fan et al Accelerated transport and maturation of lysosomal alpha-galactosidase A in Fabry lymphoblasts by an enzyme inhibitor, Nature Medicine, vol. 5, No. 1, Jan. 1999.*
Afuffo, Transient Expression of Proteins Using COS Cells, Current Protocols in Neuroscience (1998) 4.7.1-4.7.7, published by John Wiley & Sons, Inc. section entitled "Gene Cloning, Expression, and Mutagenesis".*
Wu et al., Organelle pH studies using targeted avidin and fluorescein-biotin, Chemistry & Biology 2000, 7:197-209.*
Pine et al., The Pharmacological Chaperone AT2101 Increases β-Glucocerebrosidase Levels in Macrophages and Lymphoblasts Derived From Gaucher Patients, Abstract presentation at European Human Genetics Conference Nice, France, Jun. 2007, by Amicus Therapeutics.*
Kornhaber et al., Isofagomine Induced Stabilization of Glucocerebrosidase, ChemBioChem 2008, 9, 2643-2649.*
Grabowski et al., Expression of functional human acid beta-glucosidase in COS-1 and Spodoptera frugiperda cells., Enzyme. 1989;41(3):131-42.beta.*
Alfanso, Miglustat (NB-DNJ) works as a chaperone for mutated acid h-glucosidase in cells transfected with several Gaucher disease mutations, Blood Cells, Molecules, and Diseases 35 (2005) 268-276.*
DMEM specification, DMEM Dulbecco's Modified Eagle Media, published by Life Technologies, downloaded from the internet on Sep. 8, 2014 from http://tools.lifetechnologies.com/content/sfs/productnotes/F_DMEM%20-RD-MKT-TL-HL050602.pdf.*
Fubish et al., Enzyme replacement therapy in Gaucher's disease: Large-scale purification of glucocerebrosidase suitable for human administration, Proc. Nati. Acad. Sci. USA vol. 74, No. 8, pp. 3560-3563, Aug. 1977.*
Murray et al., Purification of ,B-Glucocerebrosidase by Preparative-Scale HighPerformance Liquid Chromatography: The Use of Ethylene Glycol-Containing Buffers for Chromatography of Hydrophobic Glycoprotein Enzymes, Analytical Biochemistry 147, 301-310 (1985).*
U.S. Appl. No. 12/788,068, filed May 26, 2010.
Brillet, et al., "Using EGFP fusions to monitor the functional expression of GPCRs in the Drosophila Schneider 2 cells", Cytotechnology, 2008, 57:101-109.
International Search Report and Written Opinion for PCT/US10/036225; International Filing Date: May 26, 2010.
U.S. Appl. No. 12/788,068, Apr. 29, 2011 Non-Final Office Action.
Sara Lawrence Powers and Anne Skaja Robinson, "PDI Improves Secretion in Redox-Inactive β-Glucosidase", Biotechnol. Prog., 2007; 23: 634-369.
U.S. Appl. No. 12/788,068, Nov. 7, 2011 Non-Final Office Action.
U.S. Appl. No. 12/788,068, Jul. 29, 2011 Response to Non-Final Office Action.
Desnick, "Enzyme replacement and enhancement therapies for lysosomal disease", J. Inherit. Metab. Dis., 27: 385-410 (2004).
Fan et al., "Accelerated transport and maturation of lysosomal α-galactosidase A in Fabry lymphoblasts by an enzyme inhibitor", Nature Medicine, 5(1): 112-115 (Jan. 1999).
Ulloa-Aguirre et al., "Pharmacologic Recue of Conformationally-Defective Proteins: Implications for the Treatment of Human Disease", Traffic, 8: 821-837 (2004).
U.S. Appl. No. 12/788,068, Apr. 9, 2012 Final Office Action.
U.S. Appl. No. 12/788,068, Feb. 7, 2012 Response to Non-Final Office Action.
International Search Report and Written Opinion for PCT/US2011/061916, dated Aug. 9, 2012.
Khanna, et al., The Pharmacological Chaperone Isofagomine Increases the Activity of the Gaucher Disease L444P Mutant Form of β-Glucosidase, FEBS Journal, 277(7):1618-1638 (2010).
Yu, et al., "Pharmacological Chaperoning as a Strategy to Treat Gaucher Disease", FEBS Journal, 274:4944-4950 (2007).
U.S. Appl. No. 12/788,068, Nov. 30, 2012 Non-Final Office Action.
U.S. Appl. No. 12/788,068, Oct. 8, 2012 Amendment and Request for continued Examination (RCE).
Kakavanos, et al., "Stabilising normal and mis-sense variant α-glucosidase", FEBS Letters, 580:4365-4370 (2006).
Van Hove, et al., "High-level production of recombinant human lysosomal acid α-glucosidase in Chinese hamster ovary cells which targets to heart muscle and corrects glycogen accumulation in fibroblasts from patients with Pompe disease", PNAS, 93:65-70 (1996).
Extended European Search Report in EP10781143, dated Dec. 16, 2013, 16 pages.
Bernier, Virginie et al., Pharmacological chaperones: potential treatment for conformational diseases, Trends in Endocrinology and Metabolism, vol. 15, No. 5, Jul. 1, 2004, 222-228.
Steet, Richard A. et al., The iminosugar insofagomine increases the activity of N370S mutant acid B-glucosidase in Gaucher fibroblasts by several mechanisms, Proceedings of the National Academy of Sciences—PNAS, vol. 103, No. 37, Sep. 12, 2006, 13813-13818.

* cited by examiner

UTILIZATION OF PHARMACOLOGICAL CHAPERONES TO IMPROVE MANUFACTURING AND PURIFICATION OF BIOLOGICS

The present application is a continuation-in-part application of U.S. Ser. No. 12/788,068, filed May 26, 2010, now abandoned which claims the benefit of U.S. Provisional Application No. 61/181,255, filed May 26, 2009, both of which are hereby incorporated by reference in their entireties.

1. FIELD OF THE INVENTION

The present invention provides methods for improving the production of recombinant proteins through the use of pharmacological chaperones for the recombinant proteins. The binding of a pharmacological chaperone to a recombinant protein expressed by a cell can stabilize the protein and increase export of the protein out of the cell's endoplasmic reticulum, and increase secretion of the protein by the cell.

2. BACKGROUND

Various recombinant human proteins are produced using mammalian cell culture systems that over-express and secrete these biologics into the medium which are then purified by chromatographic processes. Successfully produced recombinant proteins include secretory proteins (e.g., blood clotting factors, immunoglobulins, erythropoietin and other hormones, elastase inhibitors, etc.) and lysosomal enzymes (e.g., β-glucocerebrosidase, α-galactosidase A, acid α-glucosidase, etc.). Several critical factors impact the efficiency and yield in such a manufacturing process: the level of expression for cell line; whether the secreted recombinant protein maintains its biological activity in the cell culture medium prior to purification; and the protein purification scheme for recovery of the biologic.

The above examples are proteins which all share a common biosynthetic pathway at the endoplasmic reticulum (ER) (Blobel et al., 1979). These proteins (which include all membrane proteins, secretory proteins, peroxisomal and lysosomal proteins) also share a common export pathway out of the ER which traffics the newly synthesized proteins to the Golgi apparatus for additional post-translational modifications to sort different classes of proteins so that they reach their intended cellular and extracellular destinations (Kornfeld, 1987). In order for these proteins to reach their final destinations, they must first fold into stable structures that sufficiently pass the ER quality control (QC) system prior to exiting this compartment (Ellgaard & Helenius, 2003). Mutant proteins often do not fold stably and are recognized by the ER QC system and retained (Ellgaard & Helenius, 2003). If these mutant proteins fail to reach a stable conformation after multiple attempts, they are ultimately eliminated by the ER-associated degradation (ERAD) systems. Aberrant ER retention of less stable mutant proteins and excessive ERAD have been shown to be the primary cause of numerous diseases including cystic fibrosis, type 2 diabetes, and various lysosomal storage diseases (Schmitz et al., 2005; Fan et al., 1999; Tropak et al., 2004).

Premature degradation of normal proteins is also observed such that an appreciable fraction of wild-type proteins fails to reach stable conformations within the allotted timeframe and ultimately eliminated by ERAD. The most cited example is the elimination of 50-70% of the wild-type cystic fibrosis transmembrane conductance regulator (CFTR) chloride ion channel. It is believed that large, complex proteins (e.g., CFTR, receptors, clotting factors, etc.) tend to fold less efficiently than smaller, simpler counterparts and are therefore prone to premature degradation. Moreover, Randall Kaufman and colleagues described the accumulation of recombinant human Factor VIII and unusual swelling of the ER, acute activation of certain kinases and various cellular pathways during the production of this biologic. These profound cellular effects are now known as ER stress associated with the expression of complex proteins and other problematic proteins (e.g., Factor VIII and Z-form alpha-1 antitrypsin). It is also believed that protein accumulation, excessive degradation and ER stress adversely affects recombinant protein production and lead to low protein yields. Thus there exists a need to improve the manufacturing process of recombinant proteins.

3. SUMMARY OF THE INVENTION

The present invention provides a method for improving the production of recombinant proteins through the use of pharmacological chaperones (also known as Active Site-Specific Chaperones; ASSCs) for the recombinant proteins. According to the invention, the production of a recombinant protein (e.g., acid α-Glucosidase, acid α-Galactosidase A, or acid β-Glucosidase) may be improved, for example, by the binding of a pharmacological chaperone (e.g., 1-deoxynorjirimycin, 1-deoxygalactonorjirimycin, or isofagomine) to a recombinant protein expressed in a host cell.

In one non-limiting embodiment, the recombinant protein is expressed by a cell line in vitro. In another non-limiting embodiment, the host cell is a mammalian cell. In another non-limiting embodiment, the host cell may be a CHO cell, HeLa cell, HEK-293 cell, 293T cell, COS cell, COS-7 cell, mouse primary myoblast, or NIH 3T3 cell.

In another non-limiting embodiment, the binding of the pharmacological chaperone to the recombinant protein increases the export of the protein out of the cell's endoplasmic reticulum.

In another non-limiting embodiment, the binding of the pharmacological chaperone to the recombinant protein increases secretion of the protein from the cell.

In another non-limiting embodiment, the binding of the pharmacological chaperone to the recombinant protein stabilizes the protein outside the cell following secretion of the protein by the cell.

In another non-limiting embodiment, the binding of the pharmacological chaperone to the recombinant protein reduces endoplasmic reticulum stress associated with the expression of the recombinant protein.

In another non-limiting embodiment, the binding of the pharmacological chaperone to the recombinant protein increases the stability of the protein at a pH greater than 5.0.

In another non-limiting embodiment, the binding of the pharmacological chaperone to the recombinant protein stabilizes the recombinant protein during purification of the protein from the cell culture media following secretion by the cell. In a further non-limiting embodiment, binding of the pharmacological chaperone to the recombinant protein during purification of the protein from the cell culture media following secretion by the cell increases the yield of the purified protein.

In another non-limiting embodiment, the binding of the pharmacological chaperone to the recombinant protein can stabilize the protein during storage. In a further non-limiting embodiment, binding of the pharmacological chaperone to the recombinant protein reduces proteolytic digestion and/or chemical damage to the protein during storage.

As used in any one of the above embodiments, the terms recombinant protein and pharmacological chaperone are used without limitation. In one non-limiting embodiment, however, the protein is an enzyme, for example, a lysosomal enzyme. In another non-limiting embodiment, the protein is acid α-Glucosidase (GAA), and the pharmacological chaperone is 1-deoxynorjirimycin (DNJ). In another non-limiting embodiment, the protein is acid α-Galactosidase A (α-Gal A), and the pharmacological chaperone is 1-deoxygalactonorjirimycin (DGJ). In another non-limiting embodiment, the protein is acid β-Glucosidase (glucocerebrosidase; Gba; GCase), and the pharmacological chaperone is isofagomine (IFG). The specified proteins and pharmacological chaperones can be employed in any one of the manufacturing methods described herein.

4. BRIEF DESCRIPTION OF THE DRAWINGS

FIG. 1 depicts the stability of recombinant human GAA (Myozyme®, Genzyme Corp.) at neutral pH (7.4) or acidic pH (5.2) in the presence or absence of 100 µM of 1-deoxynorjirimycin hydrochloride (1-DNJ-HCl) as determined in a thermal stability assay. The thermal stability assay utilizes heat to induce protein denaturation, which is monitored using a SYPRO Orange dye that fluoresces upon binding to hydrophobic amino acids (which are not exposed in a folded protein). A protein structure that requires more heat to denature is by definition more stable. Myozyme is ordinarily much more stable at lysosomal pH (5.2) than at neutral pH (7.4). However, the enzyme stability at pH 7.4 is significantly increased upon addition of 100 µM of deoxynorjirimycin, as compared to Myozyme alone.

FIG. 2A depicts the effects of 1-DNJ-HCl on recombinant human GAA (rhGAA; Myozyme®, Genzyme Corp.) activity at neutral pH (7.4) or lysosomal pH (5.2) at 37° C. GAA activity was evaluated to assess the ability of an ASSC to prolong the activity of rhGAA over time. Myozyme (45 nM) was incubated in pH 7.4 or pH 5.2 buffer with or without 50 µM 1-DNJ at 37° C. over 24 hours. Samples were assayed for GAA enzyme activity using 4-MU-α-glucose at 0, 3, 6 and 24 hours and the residual GAA activity was expressed as % of initial activity. These results indicate that 1-DNJ ameliorates the loss of GAA enzyme activity at neutral pH (7.4).

FIG. 2B depicts a parallel SYPRO Orange thermal stability experiment to determine if the loss of enzyme activity shown in FIG. 2A, particularly the loss of Myozyme activity at neutral pH (7.4), correlates with protein unfolding and denaturation. Myozyme (0.9 µM) was incubated in pH 7.4 or pH 5.2 buffer with or without 10 µM 1-DNJ-HCl at 37° C. and the protein folding was monitored every hour over 24 hours. FIGS. 2A and 2B show that GAA denaturation correlates with loss of enzyme activity. More importantly, these results indicate that 1-DNJ can prevent GAA denaturation and loss of enzyme activity at neutral pH.

FIG. 3 depicts the results of a thermal stability assay that utilizes heat to induce protein denaturation, which is monitored using a SYPRO Orange dye that fluoresces upon binding to hydrophobic amino acids (which are not exposed in a folded protein). 1-DNJ-HCl increases GAA thermostability as evident by increases in GAA's melting temperature in a dose-dependent manner. The experiment was conducted at pH 7.4.

FIG. 4 depicts the results of a thermal stability assay that utilizes heat to induce protein denaturation, which is monitored using a SYPRO Orange dye that fluoresces upon binding to hydrophobic amino acids (which are not exposed in a folded protein). Isofagomine increases acid β-glucosidase thermostability as evident by increases in melting temperature in a dose-dependent manner. The experiment was conducted at pH 7.4.

FIG. 5 depicts a SYPRO Orange thermal stability experiment to monitor the unfolding of acid β-glucosidase (GCase; Cerezyme®). GCase (2 µM) was incubated in pH 7.4 or pH 5.2 buffer with or without 10 µM IFG at 37° C. and protein unfolding was monitored every hour over 24 hours. These results indicate that IFG can prevent GCase denaturation at neutral pH.

FIG. 6 depicts the results of a thermal stability assay that utilizes heat to induce protein denaturation, which is monitored using a SYPRO Orange dye that fluoresces upon binding to hydrophobic amino acids (which are not exposed in a folded protein). 1-Deoxygalactonojirimycin increases α-Gal A (Fabrazyme®) stability in a dose-dependent manner as evident by increases in α-Gal A melting temperature. The experiment was conducted at pH 7.4.

FIG. 7 depicts the increase in acid β-glucosidase or α-Gal A activities from conditioned media of COS-7 cells during transient expression and incubation with 100 µM IFG or DGJ, respectively. These results demonstrate that incubation with a known pharmacological chaperone that binds and stabilizes a target protein causes increases in enzyme activity. The increases in enzyme activity levels are a result of increased protein secretion of the target proteins and/or the prevention of degradation and inactivation of the secreted proteins from the conditioned media. The increase in activity of acid β-glucosidase is specific for its pharmacological chaperone (IFG) since a structurally similar pharmacological chaperone (DNJ) caused no change in acid β-glucosidase activity when compared to a control transient transfection with empty vector (EV).

FIG. 8 depicts the stability of recombinant human GCase (Cerezyme®, Genzyme Corp.) at neutral pH (7.4) or acidic pH (5.2) in the presence or absence of 10 µM of IFG as determined in a thermal stability assay. The thermal stability assay utilizes heat to induce protein denaturation, which is monitored using a SYPRO Orange dye that fluoresces upon binding to hydrophobic amino acids (which are not exposed in a folded protein). A protein structure that requires more heat to denature is by definition more stable. Cerazyme is ordinarily much more stable at lysosomal pH (5.2) than at neutral pH (7.4). However, the enzyme stability at pH 7.4 is significantly increased upon addition of 10 µM of IFG, as compared to Cerazyme alone.

FIG. 9 depicts a SYPRO Orange thermal stability experiment to monitor the unfolding of acid β-glucosidase (GCase; Cerezyme®). GCase was incubated in pH 7.4 or pH 5.2 buffer with or without 10 µM or 100 µM IFG at 37° C., and protein unfolding was monitored every hour over 24 hours. These results indicate that IFG can prevent GCase denaturation at neutral pH.

FIG. 10 depicts the effects of IFG on recombinant human GCase (GCase; Cerezyme®, Genzyme Corp.) activity in human plasma at 37° C. GCase activity was evaluated to assess the ability of an ASSC to prolong the activity of GCase in human plasma over time. Cerezyme (0.5 µM) was incubated in human plasma with increasing concentrations of IFG (3 µM, 30 µM, or 100 µM) at 37° C. over 4 hours. Samples were assayed for GCase enzyme activity using 4-MU-β-glucose at 0.25, 0.5, 1, 2 and 4 hours and the residual GCase activity was expressed as % of initial activity. These results indicate that IFG ameliorates the loss of GCase enzyme activity in human plasma.

FIG. 11 depicts the increase in GCase activity from conditioned media of COS-7 cells during transient expression and incubation with IFG. These results demonstrate that incubation with a known pharmacological chaperone that binds and stabilizes a target protein causes increases in enzyme activity. The increases in enzyme activity levels are a result of increased protein secretion of the target proteins and/or the prevention of degradation and inactivation of the secreted proteins from the conditioned media. The increase in activity of GCase is specific for its pharmacological chaperone (IFG) since a structurally similar pharmacological chaperone (DGJ) caused no change in acid GCase activity when compared to a control transient transfection with empty vector (EV).

FIG. 12 depicts that DNJ had little effect on α-Glucosidase (GAA) activity from conditioned media of COS-7 cells during transient expression of GAA and incubation with DNJ.

FIG. 13 depicts the increase in α-Gal A activity from conditioned media of COS-7 cells during transient expression and incubation with DGJ. These results demonstrate that incubation with a known pharmacological chaperone that binds and stabilizes a target protein causes increases in enzyme activity. The increases in enzyme activity levels are a result of increased protein secretion of the target proteins and/or the prevention of degradation and inactivation of the secreted proteins from the conditioned media. The increase in activity of α-Gal A is specific for its pharmacological chaperone (DGJ).

5. DETAILED DESCRIPTION

Figure 1:
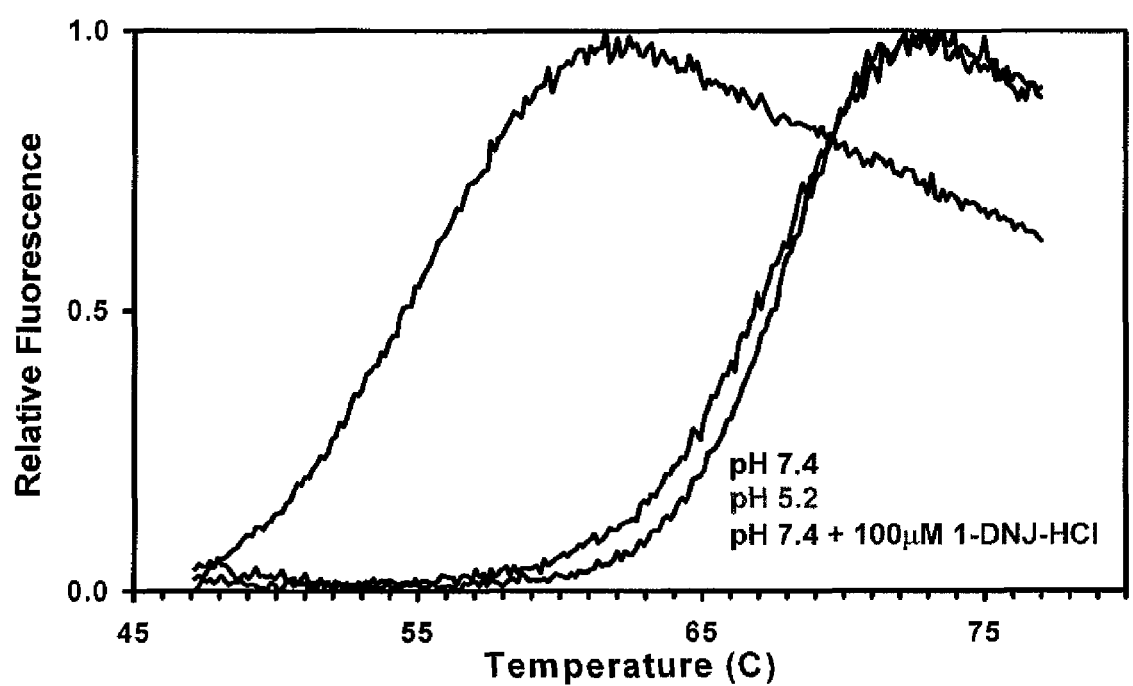

The present invention provides methods for improving the production of recombinant proteins through the use of pharmacological chaperones for the recombinant proteins. The present invention is based in part on the discovery that pharmacological chaperones can stabilize a lysosomal enzyme in a conformation which is not degraded in the endoplasmic reticulum of a cell expressing the lysosomal enzyme. The invention is also based in part on the discovery that the binding of a pharmacological chaperone to a lysosomal enzyme increases the stability of the enzyme against temperature and pH stress.

For clarity and not by way of limitation, this detailed description is divided into the following sub-portions:
(i) Definitions;
(ii) Protein deficiency disorders;
(iii) Recombinant protein production; and
(iv) In Vitro Stability.

5.1 Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

The term "enzyme replacement therapy" or "ERT" refers to refers to the introduction of a non-native, purified enzyme into an individual having a deficiency in such enzyme. The administered enzyme can be obtained from natural sources or by recombinant expression. The term also refers to the introduction of a purified enzyme in an individual otherwise requiring or benefiting from administration of a purified enzyme, e.g., suffering from protein insufficiency. The introduced enzyme may be a purified, recombinant enzyme produced in vitro, or enzyme purified from isolated tissue or fluid, such as, e.g., placenta or animal milk, or from plants.

The term "stabilize a proper conformation" refers to the ability of a compound or peptide or other molecule to associate with a wild-type protein, or to a mutant protein that can perform its wild-type function in vitro and in vivo, in such a way that the structure of the wild-type or mutant protein can be maintained as its native or proper form. This effect may manifest itself practically through one or more of (i) increased shelf-life of the protein; (ii) higher activity per unit/amount of protein; or (iii) greater in vivo efficacy. It may be observed experimentally through increased yield from the ER during expression; greater resistance to unfolding due to temperature increases (e.g. as determined in thermal stability assays), or the present of chaotropic agents, and by similar means.

As used herein, the term "active site" refers to the region of a protein that has some specific biological activity. For example, it can be a site that binds a substrate or other binding partner and contributes the amino acid residues that directly participate in the making and breaking of chemical bonds. Active sites in this invention can encompass catalytic sites of enzymes, antigen biding sites of antibodies, ligand binding domains of receptors, binding domains of regulators, or receptor binding domains of secreted proteins. The active sites can also encompass transactivation, protein-protein interaction, or DNA binding domains of transcription factors and regulators.

As used herein, the terms "pharmacological chaperone" or "active site-specific chaperone" refer to any molecule including a protein, peptide, nucleic acid, carbohydrate, etc. that specifically interacts reversibly with an active site of a protein and enhances formation of a stable molecular conformation. As used herein, "active site-specific chaperone" does not include endogenous general chaperones present in the ER of cells such as Bip, calnexin or calreticulin, or general, non-specific chemical chaperones such as deuterated water, DMSO, or TMAO.

In one non-limiting embodiment, the active site-specific chaperone may be a "competitive inhibitor" of a protein or enzyme, wherein a competitive inhibitor can refer to a compound which structurally resembles the chemical structure and molecular geometry of the enzyme substrate to bind the enzyme in approximately the same location as the substrate. Thus, the inhibitor competes for the same active site as the substrate molecule, thus increasing the Km. Competitive inhibition is usually reversible if sufficient substrate molecules are available to displace the inhibitor, i.e., competitive inhibitors can bind reversibly. Therefore, the amount of enzyme inhibition depends upon the inhibitor concentration, substrate concentration, and the relative affinities of the inhibitor and substrate for the active site.

The term "host cell" means any cell of any organism that is selected, modified, transformed, grown, or used or manipulated in any way, for the production of a substance by the cell, for example, the expression by the cell of a gene, a DNA or RNA sequence, a protein or an enzyme. In one embodiment, a host cells that is transfected with a vector encoding a protein that can be used for protein replacement therapy, for example, enzyme replacement therapy.

In another non-limiting embodiment, the host cell can be a CHO cell, HeLa cell, HEK-293 cell, 293T cell, COS cell, COS-7 cell, mouse primary myoblast, or NIH 3T3 cell.

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 95% pure; more preferably, at least 97% pure, and more preferably still at least 99% pure. Purity can be evaluated by chromatography, gel electrophoresis, immunoassay, composition analysis, biological assay, and other methods known in the art. In a specific embodiment, purified means that the level of contaminants is below a level acceptable to regulatory authorities for safe administration to a human or non-human animal.

As used herein, the terms "mutant" and "mutation" mean any detectable change in genetic material, e.g., DNA, or any process, mechanism or result of such a change. This includes gene mutations, in which the structure (e.g., DNA sequence) of a gene is altered, any gene or DNA arising from any mutation process, and any expression product (e.g., RNA, protein or enzyme) expressed by a modified gene or DNA sequence.

As used herein the term "mutant protein" refers to proteins translated from genes containing genetic mutations that result in altered protein sequences. In a specific embodiment, such mutations result in the inability of the protein to achieve its native conformation under the conditions normally present in the ER. The failure to achieve this conformation results in these proteins being degraded, rather than being transported through their normal pathway in the protein transport system to their proper location within the cell. Other mutations can result in decreased activity or more rapid turnover.

As used herein the term "wild-type gene" refers to a nucleic acid sequences which encodes a protein capable of having normal biological functional activity in vivo. The wild-type nucleic acid sequence may contain nucleotide changes that differ from the known, published sequence, as long as the changes result in amino acid substitutions having little or no effect on the biological activity. The term wild-type may also include nucleic acid sequences engineered to encode a protein capable of increased or enhanced activity relative to the endogenous or native protein.

As used herein, the term "wild-type protein" refers to any protein encoded by a wild-type gene that is capable of having functional biological activity when expressed or introduced in vivo. The term "normal wild-type activity" refers to the normal physiological function of a protein in a cell. Such functionality can be tested by any means known to establish functionality of a protein.

The term "genetically modified" refers to cells that express a particular gene product following introduction of a nucleic acid comprising a coding sequence which encodes the gene product, along with regulatory elements that control expression of the coding sequence. Introduction of the nucleic acid may be accomplished by any method known in the art including gene targeting and homologous recombination. As used herein, the term also includes cells that have been engineered to express or overexpress an endogenous gene or gene product not normally expressed by such cell, e.g., by gene activation technology.

The phrase "pharmaceutically acceptable", whether used in connection with the pharmaceutical compositions of the invention, refers to molecular entities and compositions that are physiologically tolerable and do not typically produce untoward reactions when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition.

The terms "therapeutically effective dose" and "effective amount" refer to the amount of a compound that is sufficient to result in a therapeutic response. In embodiments where an ASSC and an enzyme are administered in a complex, the terms "therapeutically effective dose" and "effective amount" may refer to the amount of the complex that is sufficient to result in a therapeutic response. A therapeutic response may be any response that a user (e.g., a clinician) will recognize as an effective response to the therapy. Thus, a therapeutic response will generally be an amelioration of one or more symptoms or sign of a disease or disorder.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 10- or 5-fold, and more preferably within 2-fold of a given value. Numerical quantities given herein are approximate unless stated otherwise, meaning that the term "about" or "approximately" can be inferred when not expressly stated.

It should be noted that a concentration of the ASSC that is inhibitory during in vitro production, transportation, or storage of the purified therapeutic protein may still constitute an "effective amount" for purposes of this invention because of dilution (and consequent shift in binding due to the change in equilibrium), bioavailability and metabolism of the ASSC upon administration in vivo.

5.2 Protein Deficiency Disorders

Disorders characterized by protein or enzyme deficiency, or loss-of-function in specific tissues, may be treatable by protein replacement therapy in theory. In such disorders, certain cells or all of the cells of an individual lack a sufficient functional protein, contain an inactive form of the protein or contain insufficient levels for biological function.

Protein or enzyme deficiency disorders may be caused, for example, by a mutation in the gene encoding the protein or enzyme which results in the expression of a protein or enzyme that is not functional, or has a reduced or altered function. The deficiency may also be caused by a mutation in the gene of the protein or enzyme that results in little to no protein or enzyme expression (e.g. a null mutation).

Further, the protein or enzyme deficiency may be due to a conformational disorder, caused by mutations that alter protein folding and retardation of the mutant protein in the ER, resulting in protein deficiency. Such diseases include, for example, but not limited to, cystic fibrosis, α1-antitrypsin deficiency, familial hypercholesterolemia, Fabry disease, Alzheimer's disease (Selkoe, Annu. Rev. Neurosci. 1994; 17:489-517), osteogenesis imperfecta (Chessler et al., J. Biol. Chem. 1993; 268:18226-18233), carbohydrate-deficient glycoprotein syndrome (Marquardt et al., Eur. J. Cell. Biol. 1995; 66: 268-273), Maroteaux-Lamy syndrome (Bradford et al., Biochem. J. 1999; 341:193-201), hereditary blindness (Kaushal et al., Biochemistry 1994; 33:6121-8), Glanzmann thrombasthenia (Kato et al., Blood 1992; 79:3212-8), hereditary factor VII deficiency (Arbini et al., Blood 1996; 87:5085-94), oculocutaneous albinism (Halaban et al., Proc. Natl. Acad. Sci. USA. 2000; 97:5889-94) and protein C deficiency (Katsumi, et al., Blood 1996; 87:4164-75). Recently, one mutation in the X-linked disease adrenoleukodystrophy (ALD), resulted in misfolding of the defective peroxisome transporter which could be rescued by low-temperature cultivation of affected cells (Walter et al., Am J Hum Genet 2001; 69:35-48). It is generally accepted that mutations take place evenly over the entire sequence of a gene. Therefore, it is predictable that the phenotype resulting from misfolding of the deficient protein exists in many other genetic disorders.

Many of the inherited protein deficient disorders are enzyme deficiencies. A large class of inherited enzyme disorders involves mutations in lysosomal enzymes and are referred to as lysosomal storage disorders (LSDs). Lysosomal storage disorders are a group of diseases caused by the accumulation of glycosphingolipids, glycogen, and mucopolysaccharides. Examples of lysosomal disorders include, but are not limited to, Gaucher disease (Beutler et al., The Metabolic and Molecular Bases of Inherited Disease, 8th ed. 2001 Scriver et al., ed. pp. 3635-3668, McGraw-Hill, New York), GM1-gangliosidosis (id. at pp 3775-3810), fucosidosis (The Metabolic and Molecular Bases of Inherited Disease 1995. Scriver, C. R., Beaudet, A. L., Sly, W. S. and Valle, D., ed pp. 2529-2561, McGraw-Hill, New York), mucopolysaccharidoses (id. at pp 3421-3452), Pompe disease (id. at pp. 3389-3420), Hurler-Scheie disease (Weismann et al., Science 1970; 169, 72-74), Niemann-Pick A and B diseases, (The Metabolic and Molecular Bases of Inherited Disease 8th ed. 2001. Scriver et al. ed., pp 3589-3610, McGraw-Hill, New York), and Fabry disease (id. at pp. 3733-3774).

Fabry Disease

The term "Fabry Disease" refers to an X-linked inborn error of glycosphingolipid catabolism due to deficient lysosomal α-galactosidase A (α-Gal A) activity. This defect causes accumulation of globotriaosylceramide (ceramide trihexoside) and related glycosphingolipids in vascular endothelial lysosomes of the heart, kidneys, skin, and other tissues.

In one non-limiting embodiment, α-galactosidase A refers to a human Gla gene which comprises a nucleic acid sequence described in GenBank Accession No. NM_000169. Alternatively α-galactosidase A can be encoded by any nucleic acid molecule exhibiting at least 50%, at least 60%, at least 70%, at least 80%, at least 90% and up to 100% homology to the α-galactosidase A gene (as determined by standard software, e.g. BLAST or FASTA), and any sequences which hybridize under standard conditions to these sequences.

In another non-limiting embodiment, human α-galactosidase A (α-GAL A) refers to an enzyme encoded by the human Gla gene, or any other amino acid sequence at least 90% homologous thereto. The human α-GAL enzyme consists of 429 amino acids and is in GenBank Accession Nos. U78027 and NP_000160.

The term "atypical Fabry disease" refers to patients with primarily cardiac manifestations of the α-GAL deficiency, namely progressive globotriaosylceramide (GL-3) accumulation in myocardial cells that leads to significant enlargement of the heart, particularly the left ventricle.

A "carrier" is a female who has one X chromosome with a defective α-GAL gene and one X chromosome with the normal gene and in whom X chromosome inactivation of the normal allele is present in one or more cell types. A carrier is often diagnosed with Fabry disease.

In one non-limiting embodiment, a pharmacological chaperone for α-galactosidase A can be 1-deoxygalactonorjirimycin (DGJ), wherein the DGJ is a compound having the following structures:

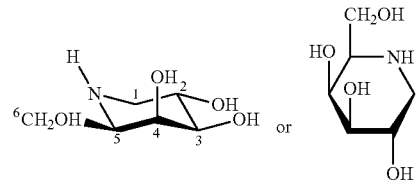

This term includes both the free base and any salt forms, and any prodrugs thereof.

Still other pharmacological chaperones for α-GAL A are described in U.S. Pat. Nos. 6,274,597, 6,774,135, and 6,599,919 to Fan et al., and include α-allo-homonojirimycin, β-1-C-butyl-deoxygalactonojirimycin, and α-galacto-homonojirimycin, calystegine $A_3$, calystegine $B_2$, calystegine $B_3$, N-methyl-calystegine $A_3$, N-methyl-calystegine $B_2$ and N-methyl-calystegine $B_3$.

Pompe Disease

Pompe disease is an autosomal recessive LSD characterized by deficient acid alpha glucosidase (GAA; α-glucosidase) activity which impairs lysosomal glycogen metabolism. The enzyme deficiency leads to lysosomal glycogen accumulation and results in progressive skeletal muscle weakness, reduced cardiac function, respiratory insufficiency, and/or CNS impairment at late stages of disease. Genetic mutations in the GAA gene result in either lower expression or produce mutant forms of the enzyme with altered stability, and/or biological activity ultimately leading to disease. (see generally Hirschhorn R, 1995, Glycogen Storage Disease Type II: Acid α-Glucosidase (Acid Maltase) Deficiency, The Metabolic and Molecular Bases of Inherited Disease, Scriver et al., eds., McGraw-Hill, New York, 7th ed., pages 2443-2464). The three recognized clinical forms of Pompe disease (infantile, juvenile and adult) are correlated with the level of residual α-glucosidase activity (Reuser A J et al., 1995, Glycogenosis Type II (Acid Maltase Deficiency), Muscle & Nerve Supplement 3, S61-S69). ASSCs (also referred to elsewhere as "pharmacological chaperones") represent a promising new therapeutic approach for the treatment of genetic diseases, such as lysosomal storage disorders (e.g. Pompe Disease).

In one non-limiting embodiment, acid alpha glucosidase (GAA) refers to a human glucosidase, alpha; acid (GAA) gene which comprises a nucleic acid sequence described in GenBank Accession Nos. NM_000152, NM_001079803, or NM_001079804. Alternatively acid alpha glucosidase can be encoded by any nucleic acid molecule exhibiting at least 50%, at least 60%, at least 70%, at least 80%, at least 90% and up to 100% homology to the acid α-glucosidase gene (as determined by standard software, e.g. BLAST or FASTA), and any sequences which hybridize under standard conditions to these sequences.

In another non-limiting embodiment, human acid α-glucosidase refers to an enzyme which hydrolyzes alpha-1,4- and alpha-1,6-linked-D-glucose polymers present in glycogen, maltose, and isomaltose. Alternative names are as follows: glucoamylase; 1,4-α-D-glucan glucohydrolase; amyloglucosidase; gamma-amylase; and exo-1,4-α-glucosidase. The human GAA gene has been mapped to chromosome 17q25.2-25.3 and has an amino acid sequence described in GenBank Accession Nos. Y00839, NP_000143, NP_001073271, or N_001073272, or any other amino acid sequence at least 90% homologous thereto.

Infantile Pompe disease (type I or A) is most common and most severe, characterized by failure to thrive, generalized hypotonia, cardiac hypertrophy, and cardiorespiratory failure within the second year of life. Juvenile Pompe disease (type II or B) is intermediate in severity and is characterized by a predominance of muscular symptoms without cardiomegaly. Juvenile Pompe individuals usually die before reaching 20 years of age due to respiratory failure. Adult Pompe disease (type III or C) often presents as a slowly progressive myopathy in the teenage years or as late as the sixth decade (Felice K J et al., 1995, Clinical Variability in Adult-Onset Acid Maltase Deficiency: Report of Affected Sibs and Review of the Literature, Medicine 74, 131-135).

In Pompe, it has been shown that α-glucosidase is extensively modified post-translationally by glycosylation, phosphorylation, and proteolytic processing. Conversion of the 110 kilodalton (kDa) precursor to 76 and 70 kDa mature forms by proteolysis in the lysosome is required for optimum glycogen catalysis.

As used herein, the term "Pompe Disease" refers to all types of Pompe Disease. The formulations and dosing regimens disclosed in this application may be used to treat, for example, Type I, Type II or Type III Pompe Disease.

In one particular non-limiting embodiment, a pharmacological chaperone for acid α-glucosidase can be 1-deoxynorjirimycin (1-DNJ), which is represented by the following formula:

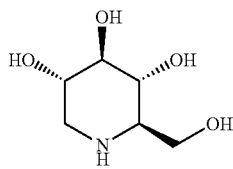

or a pharmaceutically acceptable salt, ester or prodrug thereof. In one embodiment, the salt is hydrochloride salt (i.e. 1-deoxynorjirimycin-HCl).

Still other pharmacological chaperones for acid α-glucosidase are described in U.S. Pat. No. 6,599,919 to Fan et al., and U.S. Patent Application Publication No. 2006/0264467 to Mugrage et al., and include α-homonojirimycin and castanospermine.

Gaucher Disease

As used herein, the term "Gaucher Disease" refers to a deficiency of the lysosomal enzyme glucocerebrosidase that breaks down fatty glucocerebrosides. The fat then accumulates, mostly in the liver, spleen and bone marrow. Gaucher disease can result in pain, fatigue, jaundice, bone damage, anemia and even death. There are three clinical phenotypes of Gaucher disease. Patients with, Type 1 manifest either early in life or in young adulthood, bruise easily and experience fatigue due to anemia, low blood platelets, enlargement of the liver and spleen, weakening of the skeleton, and in some instances have lung and kidney impairment. There are no signs of brain involvement. In Type II, early-onset, liver and spleen enlargement occurs by 3 months of age and there is extensive brain involvement. There is a high mortality rate by age 2. Type III is characterized by liver and spleen enlargement and brain seizures. The β-glucocerebrosidase gene is located on the human 1q21 chromosome. Its protein precursor contains 536 amino acids and its mature protein is 497 amino acids long.

In one non-limiting embodiment, glucocerebrosidase refers to a Homo sapiens glucosidase, beta (Gba) gene which comprises a nucleic acid sequence described in GenBank Accession Nos. NM_001005741, NM_001005741, NM_001005749, NM_001005750, or NM_000157. Alternatively glucocerebrosidase can be encoded by any nucleic acid molecule exhibiting at least 50%, at least 60%, at least 70%, at least 80%, at least 90% and up to 100% homology to the glucocerebrosidase gene (as determined by standard software, e.g. BLAST or FASTA), and any sequences which hybridize under standard conditions to these sequences.

In another non-limiting embodiment, glucocerebrosidase refers to an enzyme encoded by the human glucosidase, beta (Gba) gene (GenBank Accession Nos. NP_001005741, NP_001005742, NP_001005749, NP_001005750, or NP_000148), or any other amino acid sequence at least 90% homologous thereto.

In one non-limiting embodiment, a pharmacological chaperone for glucocerebrosidase can be isofagomine (IFG; (3R,4R,5R)-5-(hydroxymethyl)-3,4-piperidinediol), having the following structure:

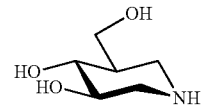

Isofagomine tartrate has recently been described in commonly-owned U.S. Pat. No. 7,501,439 to Mugrage et al., and has been assigned CAS number 919364-56-0. Isofagomine also may be prepared in the form of other acid addition salts made with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrate, phosphate, borates, citrates, benzoates, ascorbates, salicylates and the like). Such salts can be formed as known to those skilled in the art.

Still other pharmacological chaperones for glucocerebrosidase are described in U.S. Pat. No. 6,599,919 to Fan et al., U.S. Pat. No. 6,046,214 to Kristiansen et al., U.S. Pat. No. 5,844,102 to Sierks et al., and U.S. Patent Application Publication No. 2008/0009516 to Wustman, and include C-benzyl isofagomine and derivatives, N-alkyl (C9-12)-DNJ, Glucoimidazole (and derivatives), C-alkyl-IFG (and derivatives), N-alkyl-β-valeinamines, fluphenozine, N-Dodecyl-DNJ and calystegines $A_3$, $B_1$, $B_2$ and $C_1$.

In addition to inherited disorders, other enzyme deficiencies arise from damage to a tissue or organ resulting from primary or secondary disorders. For example, damaged pancreatic tissue, or pancreatitis, is caused by alcoholism results in a deficiency in pancreatic enzymes necessary for digestion. Pancreatitis is currently being treated using enzyme replacement therapy.

Disorders of protein deficiency may treated by administration of replacement proteins to enhance or stimulate biological processes. For example, individuals with anemia are administered recombinant erythropoietin (EPOGEN®, PROCRIT®, EPOIETIN®) to stimulate red blood cell production and increase oxygen transportation to tissues. In addition, recombinant interferons such as interferon alpha 2b (INTRON A®, PEG-INTRON®, or REBETOL®), and interferon beta 1a (AVONEX®, BETASERON®) are administered to treat hepatitis B and multiple sclerosis, respectively. Still other proteins administered are recombinant human deoxyribonuclease I (rhDNase-PULMOZYME®), an enzyme which selectively cleaves DNA used to improve pulmonary function in patients with cystic fibrosis; recombinant thyroid stimulating hormone (THYROGEN®) developed for use in thyroid cancer patients who have had near-total or total thyroidectomy, and who must therefore take thyroid hormones; recombinant G-CSF (NEUPOGEN®) for treating neutropenia from chemotherapy, and digestive enzymes in individuals with pancreatitis. Another significant area of protein therapy is in the treatment of infectious diseases and cancer with antibodies, which have a highly specific, well-defined active site. Antibody therapeutic products include RESPIRGRAM® for respiratory syncitial virus, HERCEPTIN®, for breast cancer; REMICAID® and HUMIRA®, for arthritis and inflammatory diseases, and others. ASSCs for antibodies are well known, and either the target antigen or a structurally related analog (e.g., a modified form of the active target or a mimetic) can be employed.

A "patient" refers to a subject who has been diagnosed with or is suspected of having a particular disease. The patient may be human or animal. For example, a "Fabry disease patient" refers to an individual who has been diagnosed with or suspected of having Fabry disease and has a mutated α-GAL. Characteristic markers of Fabry disease can occur in male hemizygotes and female carriers with the same prevalence, although females typically are less severely affected.

5.3 Recombinant Protein Production

The replacement proteins useful for treating patients with a protein deficiency, for example, through enzyme replacement therapy, can be isolated and purified using ordinary molecular biology, microbiology, and recombinant DNA techniques within the skill of the art. For example, nucleic acids encoding the replacement protein can be isolated using recombinant DNA expression as described in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J, Higgins, eds. (1984)); Animal Cell Culture (R. I. Freshney, ed. (1986)); Immobilized Cells And Enzymes (IRL Press, (1986)); B. E Perbal, A Practical Guide To Molecular Cloning (1984); F. M. Ausubel et al. (eds.), Current Protocols in Molecular Biology, John Wiley & Sons, Inc. (1994). The nucleic acid encoding the protein may be full-length or truncated, as long as the gene encodes a biologically active protein. For example, a biologically active, truncated form of α-Gal A, the defective enzyme associated with Fabry disease, has been described in U.S. Pat. No. 6,210,666 to Miyamura et al.

The identified and isolated gene encoding the target protein can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, E. coli, bacteriophages such as lambda derivatives, or plasmids such as pBR322 derivatives or pUC plasmid derivatives, e.g., pGEX vectors, proal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Production of the recombinant protein can be maximized by genetic manipulations such as including a signal peptide at the N terminus to facilitate secretion or a 3' untranslated sequence containing a polyadenylation site.

In one non-limiting embodiment, the constructs used to transduce host cells are viral-derived vectors, including but not limited to adenoviruses, adeno-associated viruses, herpes virus, mumps virus, poliovirus, retroviruses, Sindbis virus and vaccinia viruses.

Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., E. coli, and facile purification for subsequent insertion into an appropriate expression cell line, if such is desired.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used. Different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed, such as glycosylation, sialyation and phosphorylation. For example, expression in a bacterial system can be used to produce a nonglycosylated core protein product. However, protein expressed in bacteria may not be properly folded. Expression in yeast can produce a glycosylated product. Expression in eukaryotic cells can increase the likelihood of "native" glycosylation and folding of a heterologous protein. Moreover, expression in mammalian cells can provide a tool for reconstituting, or constituting, protein.

Purification of recombinantly expressed protein can be achieved using methods known in the art such as by ammonium sulfate precipitation, column chromatography containing hydrophobic interaction resins, cation exchange resins, anion exchange resins, and chromatofocusing resins. Alternatively, immunoaffinity chromatography can be used to purify the recombinant protein using an appropriate polyclonal or monoclonal antibody that binds specifically to the protein, or to a tag that is fused to the recombinant protein. In a preferred embodiment, the purity of the recombinant protein used for the method of the present invention will be at least 95%, preferably at least 97% and most preferably, greater than 98%.

In other non-limiting embodiments, the replacement proteins useful for treating patients with a protein deficiency, for example, through enzyme replacement therapy, may be purified from a recombinant cellular expression system (e.g., mammalian cells or insect cells-see generally U.S. Pat. No. 5,580,757 to Desnick et al.; U.S. Pat. Nos. 6,395,884 and 6,458,574 to Selden et al.; U.S. Pat. No. 6,461,609 to Calhoun et al.; U.S. Pat. No. 6,210,666 to Miyamura et al.; U.S. Pat. No. 6,083,725 to Selden et al.; U.S. Pat. No. 6,451,600 to Rasmussen et al.; U.S. Pat. No. 5,236,838 to Rasmussen et al.; and U.S. Pat. No. 5,879,680 to Ginns et al.), human placenta, or animal milk (see U.S. Pat. No. 6,188,045 to Reuser et al.).

Other synthesis techniques for obtaining the replacement protein suitable for pharmaceutical use may be found, for example, in U.S. Pat. Nos. 7,423,135, 6,534,300, and 6,537,785; International Published Application No. 2005/077093 and U.S. Published Application Nos. 2007/0280925, and 2004/0029779. These references are hereby incorporated by reference in their entireties for all purposes.

Furthermore, different vector/host expression systems may affect processing reactions, such as proteolytic cleavages, to a different extent. The expression efficiency can be increased by use of a specific chaperone, as described in U.S. Pat. No. 6,274,597, and related family members.

As noted above, one aspect of the present invention provides a method for improving the production of a recombinant protein, which method comprises contacting a host cell that expresses a recombinant protein with a pharmacological chaperone specific for the recombinant protein.

In one non-limiting embodiment, the pharmacological chaperone may stabilize a target recombinant protein in the ER of a cell expressing the protein, and prevent ERAD and premature degradation of the protein. In doing so, the pharmacological chaperone may reduce ER stress associated with the expression of the recombinant protein which in turn, may allow the production cell line to maintain high viability and expression of the protein.

In other non-limiting embodiments, the pharmacological chaperone may stabilize a recombinant protein expressed by a cell, and increase export of the protein out of the cell's ER, and increase secretion of the protein out of cell.

In other non-limiting embodiments, the pharmacological chaperone may stabilize a target recombinant protein outside a cell expressing the protein (i.e., after the protein has been secreted into the cell culture medium). By stabilizing the recombinant protein, the pharmacological chaperone may confer a benefit to proteins that normally must be stored at a lower pH to preserve stability, and are not usually stable in most cell culture media which are typically formulated at neutral pH. Significant losses in enzyme activity can result while these proteins remain in the cell culture media prior to harvest and purification. Pharmacological chaperones can stabilize these proteins and prevent irreversible denaturation and inactivation of protein activity in media with a pH greater than 5.0, for example, at a neutral pH.

In other non-limiting embodiments, the pharmacological chaperone may protect a target recombinant protein during purification of the protein from cell culture media. If a recombinant protein is not stable in medium, it may denature and be susceptible to proteolysis by contaminating proteases in the purification mixtures. Pharmacological chaperones may prevent this proteolysis by stabilizing the protein and preventing proteolytic sites from being revealed. The pharmacological chaperone may therefore improve protein integrity and/or enzyme activity during the purification process.

In other non-limiting embodiments, the pharmacological chaperone may protect a recombinant protein during storage and/or preparation of a pharmaceutical formulation. For example, a pharmacological chaperone can bind and inhibit enzyme activity of clotting factors (e.g. proteases) to ensure that such proteins are proteolytically digested during storage and formulation. Pharmacological chaperones may also prevent other types of irreversible chemical damage (e.g., oxidation, hydrolysis or deamidation), or physical instability, such as aggregation, precipitation and adsorption to surfaces, during formulation. In addition, the pharmacological chaperone may stabilize and protect the protein from stresses such as pH, temperature, shear stress, freeze/thaw stress and combinations of these stresses, which may otherwise contribute to the protein's degradation.

In one, non-limiting embodiment, the replacement protein is a recombinant acid α-glucosidase (GAA), encoded by the most predominant of nine observed haplotypes of this gene and is produced by recombinant DNA technology in a Chinese hamster ovary cell line. The recombinant GAA can be for example, a recombinant GAA as described in Kakkis et al., 2008, "An improved alpha-glucosidase enzyme for Pompe disease," Abstract, 58th Annual Meeting of the ASHG; Kishnani et al., 2007, Neurology. 68(2):99-109; U.S. Pat. No. 6,118,045 to Reuser et al., U.S. Pat. No. 7,056,712 to Chen, and U.S. Pat. No. 7,351,410 to van Bree, each of which is incorporated by reference in their entireties for all purposes.

In other preferred non-limiting embodiments, the ASSC is 1-deoxynorjirimycin (1-DNJ) and the GAA is a recombinant GAA. In an alternative embodiment, the ASSC is α-homonojirimycin and the GAA is a recombinant GAA. In another alternative embodiment the ASSC is castanospermine and the GAA is a recombinant GAA. The ASSC (e.g. 1-deoxynorjirimycin, α-homonojirimycin and castanospermine) may be obtained from synthetic libraries (see, e.g., Needels et al., Proc. Natl. Acad. Sci. USA 1993; 90:10700-4; Ohlmeyer et al., Proc. Natl. Acad. Sci. USA 1993; 90:10922-10926; Lam et al., PCT Publication No. WO 92/00252; Kocis et al., PCT Publication No. WO 94/28028) which provide a source of potential ASSC's according to the present invention. Synthetic compound libraries are commercially available from Maybridge Chemical Co, (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from e.g. Pan Laboratories (Bothell, Wash.) or MycoSearch (NC), or are readily producible. Additionally, natural and synthetically produced libraries and compounds are readily modified through Res. 1986; 155:119-29.

5.4 In Vitro Stability

Ensuring the stability of a replacement protein formulation during its shelf life is a major challenge. For example, vials of recombinant enzyme are often for single use only and unused product should be discarded. Additionally, recombinant enzyme often must often be reconstituted, diluted, and administered by a health care professional, and that administration should be without delay. Recombinant enzymes must often be stored at low temperatures, for example, 2 to 8° C., and the product only stable for a limited amount of time, for example, up to 24 hours.

When the ASSC and the replacement protein are present in the same composition, the formulated compositions of the invention provide more stable compositions. In addition to stabilizing the administered protein in vivo, the ASSC reversibly binds to and stabilizes the conformation of the replacement protein in vitro, thereby preventing aggregation and degradation, and extending the shelf-life of the formulation. Analysis of the ASSC/replacement protein interaction may be evaluated using techniques well-known in the art, such as, for example, differential scanning calorimetry, or circular dichroism.

For example, where an aqueous injectable formulation of the composition is supplied in a stoppered vial suitable for withdrawal of the contents using a needle and syringe, the presence of an ASSC inhibits aggregation of the replacement protein. The vial could be for either single use or multiple uses. The formulation can also be supplied as a prefilled syringe. In another embodiment, the formulation is in a dry or lyophilized state, which would require reconstitution with a standard or a supplied, physiological diluent to a liquid state. In this instance, the presence of an ASSC would stabilize the replacement protein during and post-reconstitution to prevent aggregation. In the embodiment where the formulation is a liquid for intravenous administration, such as in a sterile bag for connection to an intravenous administration line or catheter, the presence of an ASSC would confer the same benefit.

In addition to stabilizing the replacement protein to be administered, the presence of an ASSC may enable the replacement protein formulation to be stored at a neutral pH of about 7.0-7.5. This will confer a benefit to proteins that normally must be stored at a lower pH to preserve stability. For example, lysosomal enzymes, such as GAA, typically retain a stable conformation at a low pH (e.g., 5.0 or lower). However, extended storage of the replacement enzyme at a low pH may expedite degradation of the enzyme and/or formulation.

6. EXAMPLES

The present invention is further described by means of the examples, presented below. The use of such examples is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification. The invention is therefore to be limited only by the terms of the appended claims along with the full scope of equivalents to which the claims are entitled

Example 1

Acid α-Glucosidase Stability Upon Thermal Challenge

The stability of recombinant human GAA (Myozyme®, Genzyme Corp.) with and without 100 µM of the ASSC 1-deoxynorjirimycin hydrochloride (DN.1) was determined via a thermal stability assay that utilizes heat to induce protein denaturation. Denaturation is monitored using a SYPRO Orange dye that fluoresces upon binding to hydrophobic amino acids (which are not exposed in a folded protein).

The thermal stability was performed at pH 7.4 for two formulations, which corresponds to the pH of the ER. As shown in FIG. 1, the formulation that contains 100 µM of DNJ at pH 7.4 required significantly more heat to denature, and is thus more stable, as compared to formulation without the ASSC at pH 7.4.

Example 2

1-Deoxynorjirimycin (DNJ) Prevents Acid α-Glucosidase Activity Loss Upon Extended Incubation at 37° C.

Residual GAA activity was determined for four formulations:
(1) Myozyme alone at pH 7.4;
(2) Myozyme plus 50 µM DNJ at pH 7.4;
(3) Myozyme alone at pH 5.2;
(4) Myozyme plus 50 µM DNJ at pH 5.2.

Activity was measured, based on the % of initial activity (t=0) over 24 hours. Samples were assayed for GAA enzyme activity based on the hydrolysis of the fluorogenic substrate 4-MU-α-glucose at 0, 3, 6 and 24 hours. The GAA activity was expressed as % of initial activity, i.e. residual activity.

Figure 2A:
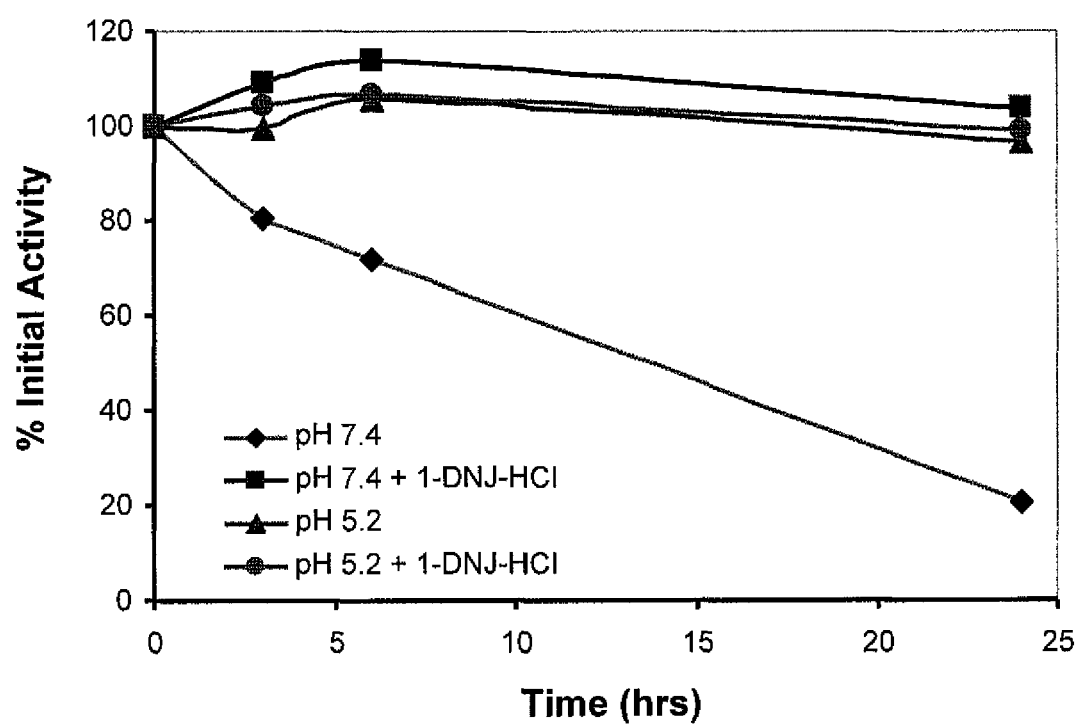

As shown in FIG. 2A, formulation (1) above (without the ASSC) lost activity over time, having only about 20% of its initial activity 24 hours after administration. In contrast, formulation (2) maintained most, if not all of its initial activity over 24 hours. Both formulations at ph 5.2 (formulations (3) and (4) above) maintained most of their initial activity over 24 hours.

Figure 2B:
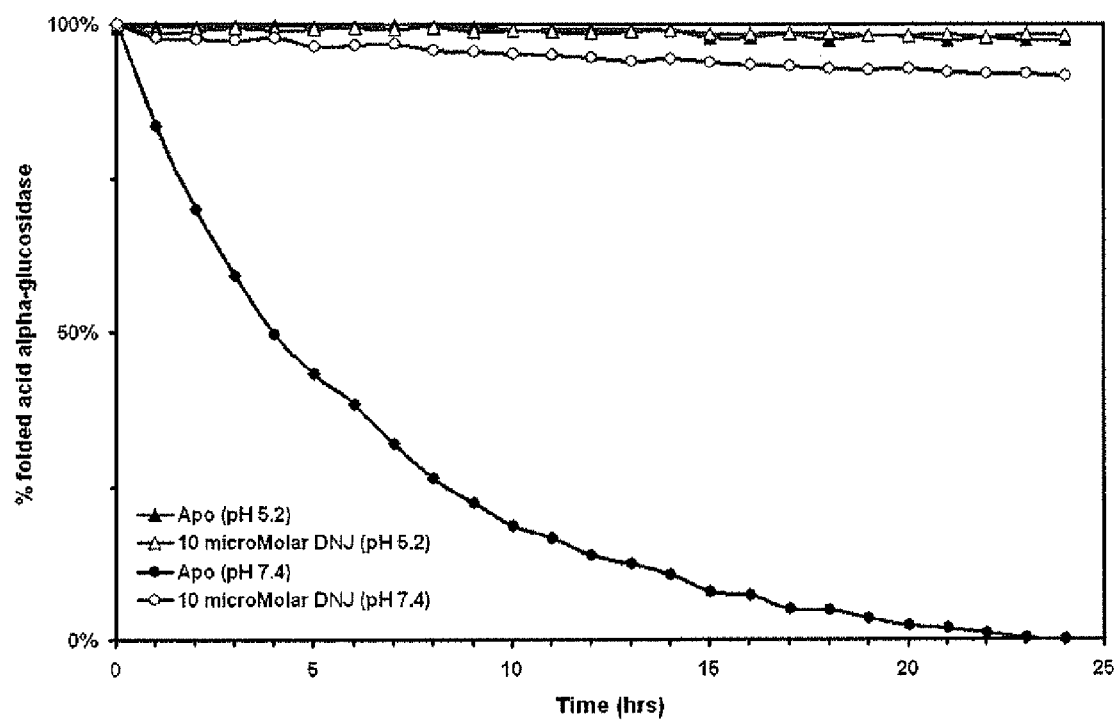

In order to determine if loss of initial enzyme activity is correlated to failure to maintain a proper conformation, a SYPRO Orange thermal stability experiment was performed on the samples above as generally described in Example 1. In this thermal stability experiment, the concentration of DNJ was decreased to 10 µM in formulations (2) and (4). Based on this experiment, the % of folded GAA was estimated and plotted in FIG. 2B. The decrease in the amount of folded GAA over 24 hours in FIG. 2B for the formulation (1) correlates to the loss of activity shown in FIG. 2A for this same general formulation.

Example 3

DNJ Increases GAA Stability Upon Thermal Challenge

Figure 3:
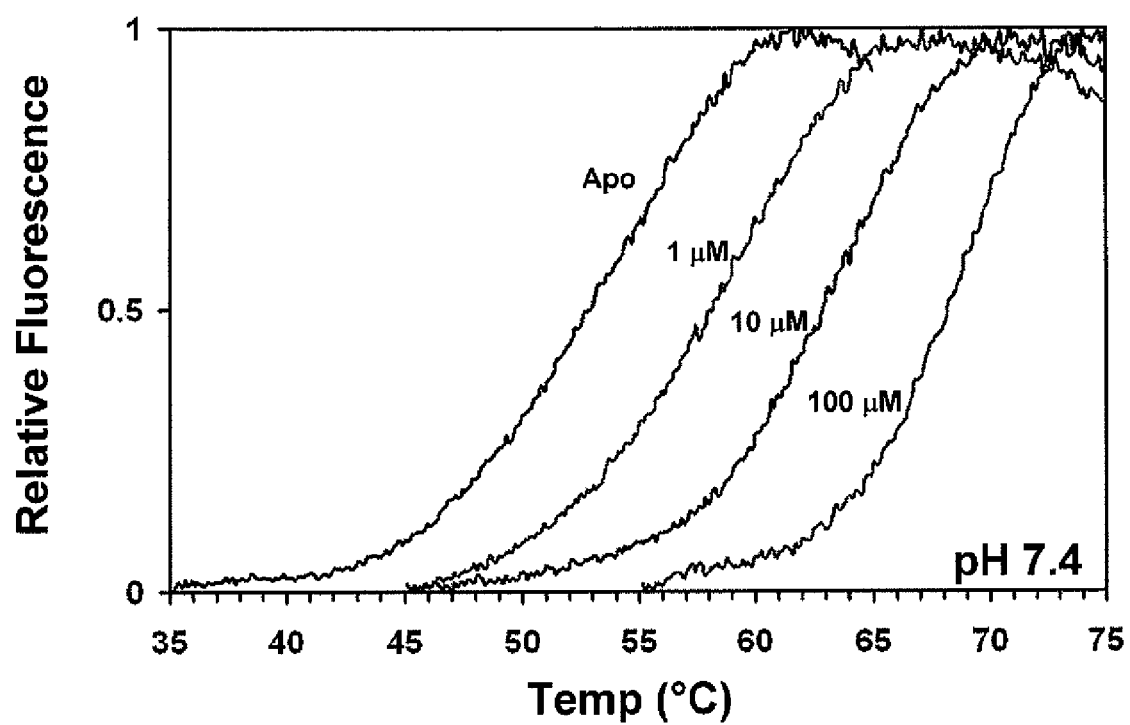

A thermal stability experiment as generally described in Example 1 was performed on four compositions:
(1) Myozyme only composition;
(2) Myozyme plus 1 µM of 1-DNJ-HCl;
(3) Myozyme plus 10 µM of 1-DNJ-HCl;
(4) Myozyme plus 100 µM of 1-DNJ-HCl;

As shown in FIG. 3, DNJ-HCl increases GAA thermostability as evident by increases in GAA's melting temperature in a dose-dependent manner.

Example 4

Isofagomine (IFG) Increases Acid β-Glucosidase Stability Upon Thermal Challenge

A thermal stability experiment as generally described in Example 1 was performed on three compositions of GCase (Cerezyme®):

(1) GCase only composition; pH 7.4
(2) GCase plus 10 µM of IFG; pH 7.4
(3) GCase plus 100 µM of IFG; pH 7.4

Figure 4:
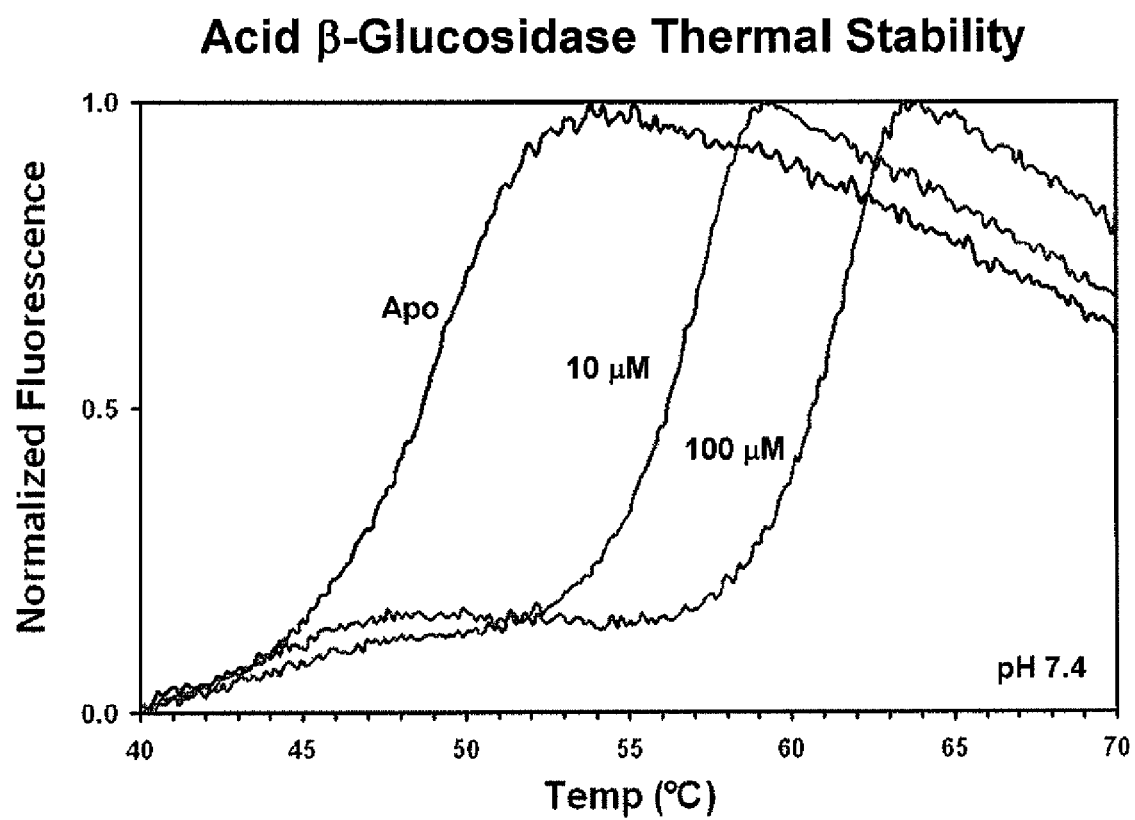

As shown in FIG. 4, IFG increases GCase thermal stability in a dose-dependent manner as evident by increases in the protein's melting temperature.

Example 5

GCase Thermal Stability in the Presence of IFG

Percent of unfolded GCase was determined for three formulations:
(1) GCase alone at pH 5.2
(2) GCase alone at pH 7.4;
(3) GCase with 10 µM IFG; pH 7.4

Figure 5:
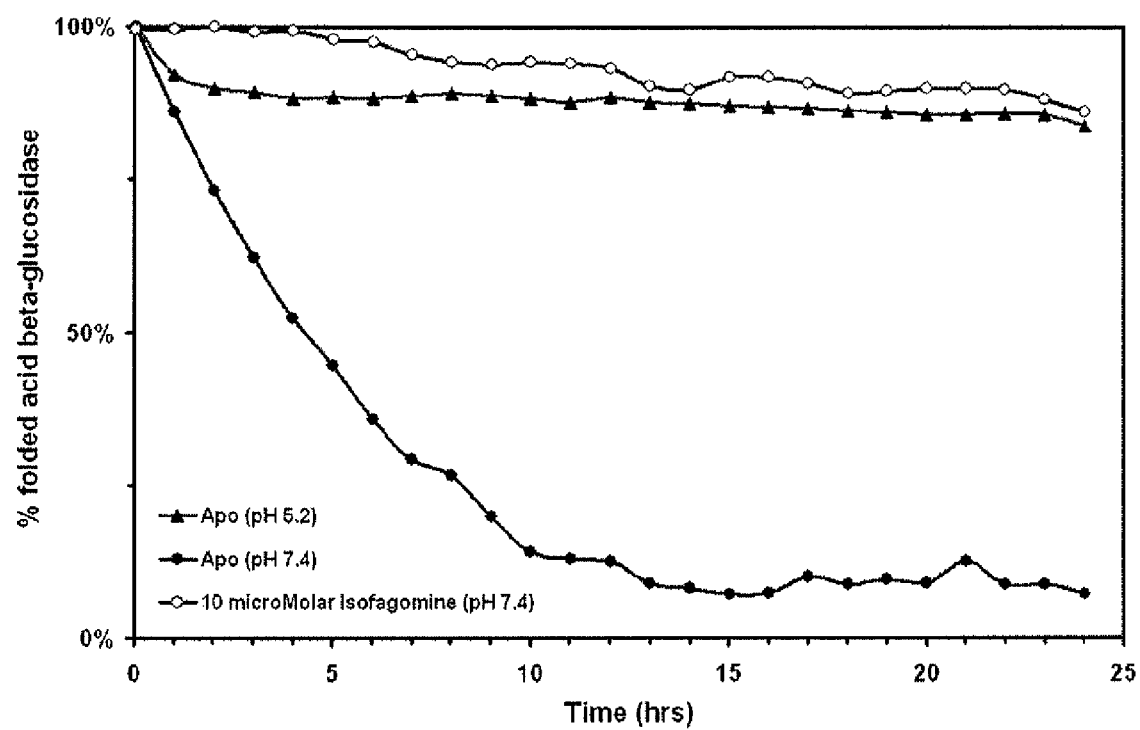

To determine if IFG prevented GCase unfolding at 37° C. and neutral pH, a SYPRO Orange thermal stability experiment was performed on the samples above as generally described in Example 1. In this thermal stability experiment, the concentration of IFG was 10 µM in formulation (3). Based on the results in FIG. 5, IFG prevented GCase unfolding under the specified conditions.

Example 6

1-Deoxygalactonorijirimycin (DGJ) Increases α-Gal A Stability Upon Thermal Challenge A thermal stability experiment as generally described in Example 1 was performed on three compositions of α-Gal A (Fabrazyme®):
(1) α-Gal A only composition; pH 7.4
(2) α-Gal A plus 10 µM of DGJ; pH 7.4
(3) α-Gal A plus 100 µM of DGJ; pH 7.4

Figure 6:
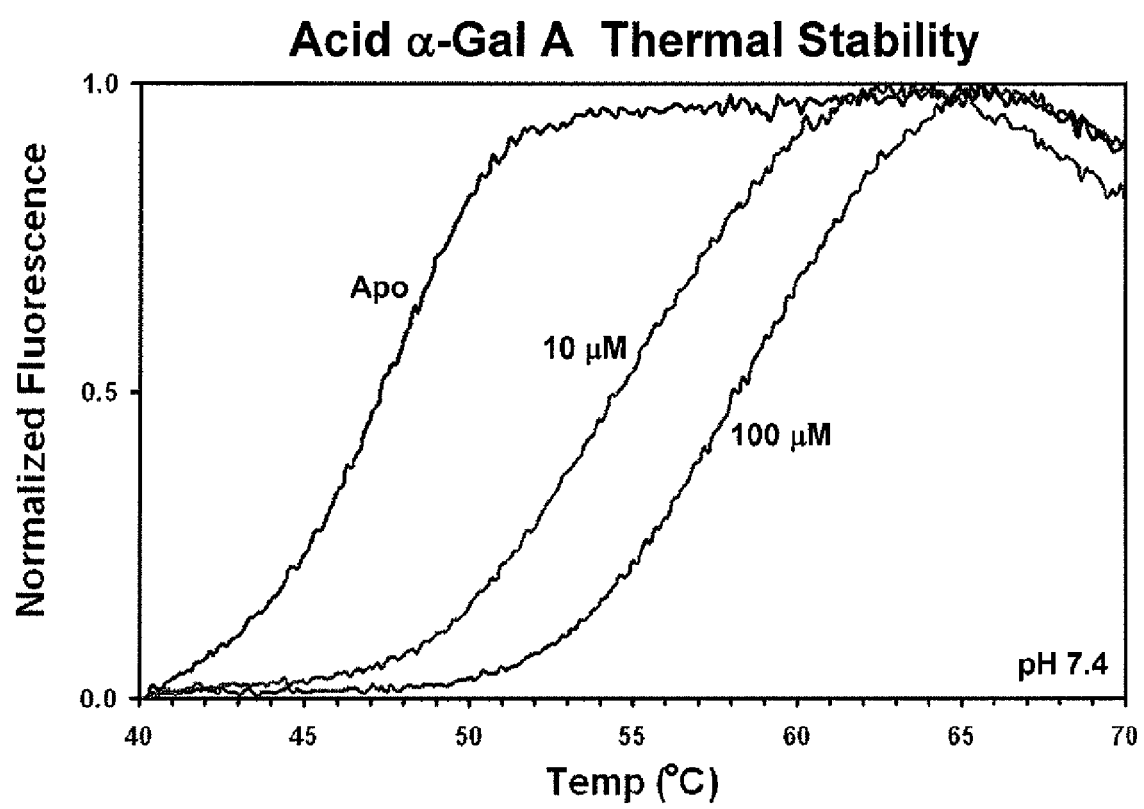

As shown in FIG. 6, DGJ increases α-Gal A thermal stability in a dose-dependent manner as evident by increases in the protein's melting temperature.

Example 7

Pharmacological Chaperones Increase Recombinant Protein Activity Levels from Transiently-Transfected COS-7 Cells COS-7 cells were transiently transfected with empty vector, a plasmid coding for the GBA gene, or a plasmid coding for the GLA gene. The various transient transfections were incubated with 100 µM of the indicated pharmacological chaperones (IFG, DGJ or DNJ). After 48-hours of protein expression, the conditioned media from each transfection was harvested, and the level of acid β-glucosidase or α-Gal A activities were assessed after capture of secreted proteins with concanavalin A-agarose beads. This concanavalin A capture step was necessary to eliminate potential inhibition of enzyme activities by the pharmacological chaperones during the course of activity determination using the appropriate fluorogenic substrates (4-MU-β-glucose for GCase; 4-MU-β-galactose for α-Gal A).

Figure 7:
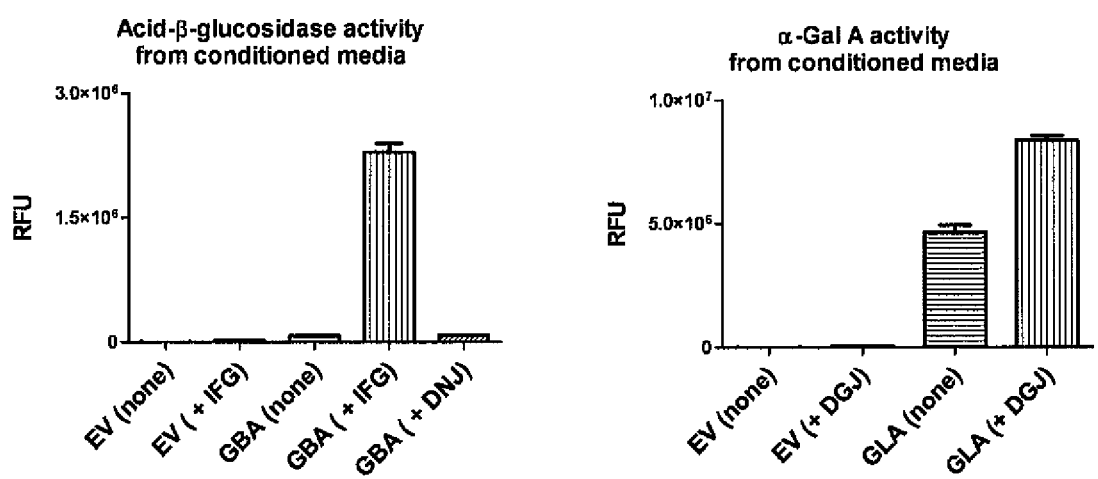

As shown in FIG. 7, incubation with IFG or DGJ increased the activities of acid β-glucosidase or α-Gal A, respectively. When DNJ was included in the transient expression of acid β-glucosidase, no increase in enzyme activity was seen. This observation indicates that increases in enzyme activity is due to specific interactions with a protein's known pharmacological chaperone and/or inhibitor.

Example 8

Isofagomine (IFG) Increases Acid β-Glucosidase Stability Upon Thermal Challenge

A thermal stability experiment as generally described in Examples 1 and 4 was performed on three compositions of GCase (Cerezyme®):
(1) GCase only composition; pH 7.4
(2) GCase only composition; pH 5.2
(3) GCase plus 10 µM of IFG; pH 7.4

Protein denaturation was monitored using SYPRO Orange dye which fluoresces when bound to exposed hydrophobic amino acids.

Figure 8:
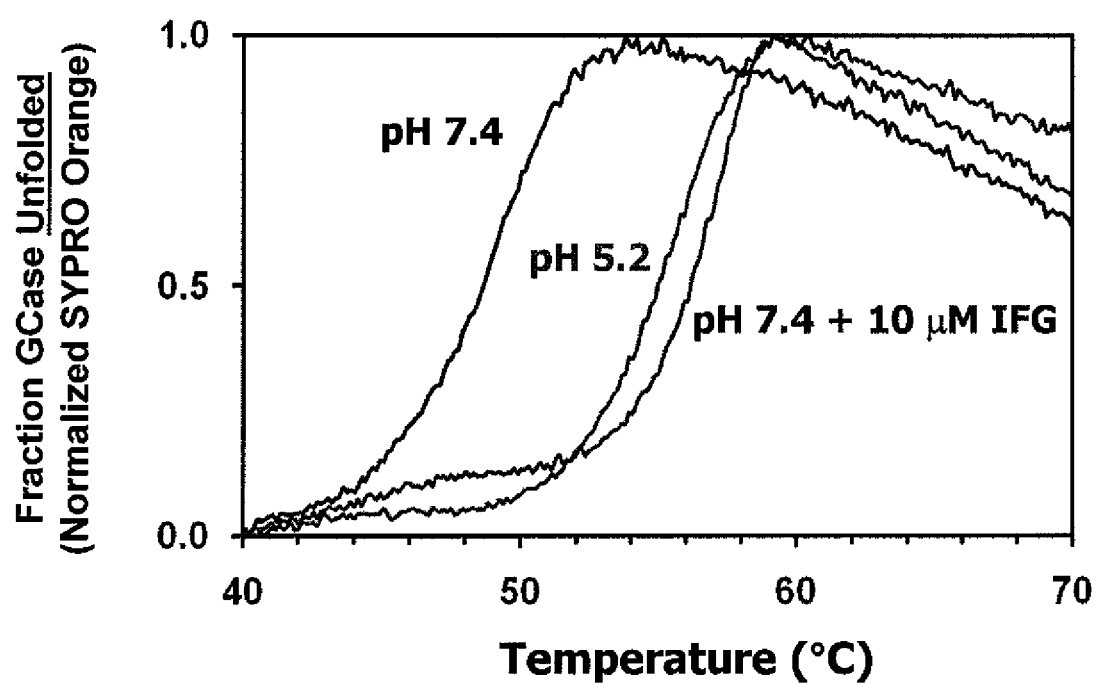

As shown in FIG. 8, GCase was more stable at acidic (lysosomal) pH than at neutral pH (Endoplasmic Reticulum/blood). IFG significantly increases stability of recombinant human GCase at neutral pH.

Example 9

GCase Thermal Stability in the Presence of IFG

Percent of unfolded GCase (Cerezyme®) was determined for the following formulations:
(1) GCase alone at pH 5.2
(2) GCase with 10 µM IFG; pH 7.4;
(3) GCase with 100 µM IFG; pH 5.2
(4) GCase with 100 µM IFG; pH 7.4

Figure 9:
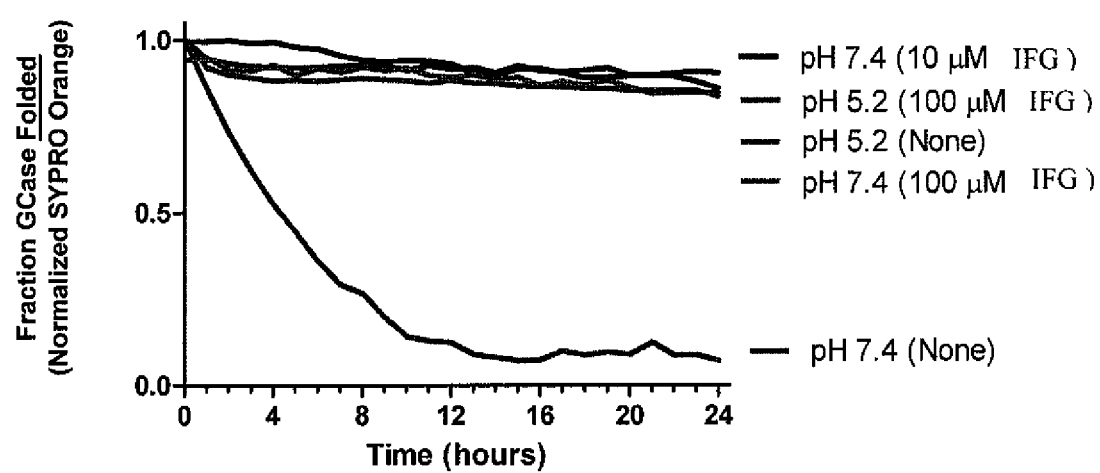

To determine if IFG prevented GCase unfolding at 37° C. and neutral pH, a SYPRO Orange thermal stability experiment was performed on the samples above as generally described in Examples 1 and 5. In this thermal stability experiment, the concentration of IFG was 0, 10 µM, or 100 µM as described above. A shown in FIG. 9, GCase protein has a half-life of about 3.5 hours in neutral pH buffer. IFG significantly increases the stability of GCase at neutral pH at concentrations of 10 µM and 100 µM.

Example 10

GCase Stability in Human Plasma in the Presence of IFG

Figure 10:
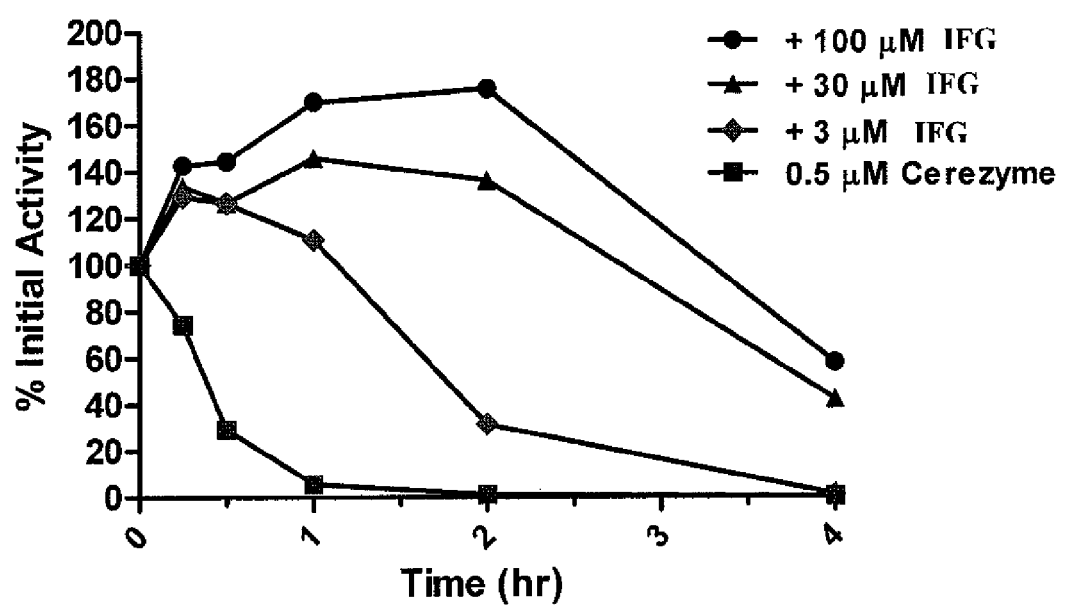

The activity of GCase (0.5 µM; Cerazyme®) at 37° C. in human plasma was assessed for increasing concentrations of IFG (3 µM, 30 µM, and 100 µM) as a function time using the substrate 4-MUG. As shown in FIG. 10, most GCase is inactivated within 30 minutes, and completely inactive by 1 hour. However, IFG significantly increases the stability of GCase and prevents enzyme inactivation.

Example 11

IFG Increases the Recovery of Functional GCase from Conditioned Media

COS-7 cells were transiently transfected with human GBA1 plasmid encoding the GCase gene. The various transient transfections were incubated with no pharmacological chaperone, DGJ, IFG or AT3375. After 72-hours of protein expression, the conditioned media from each transfection was harvested, and the level of GCase activity was assessed using the GCase substrate 4-MU-β-glucose.

Figure 11:
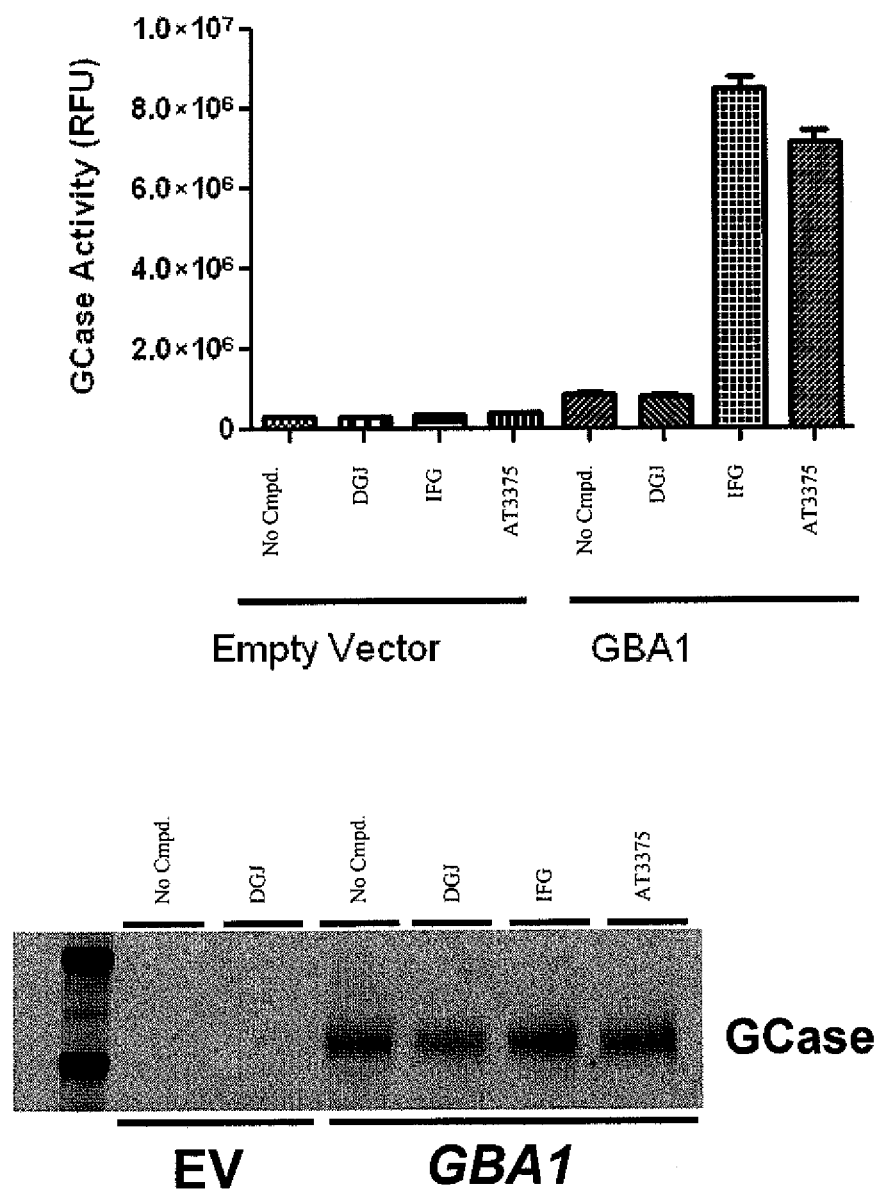

As shown in FIG. 11, incubation with IFG or AT3375 increased the activity of GCase recovered from the media. When DGJ was included in the transient expression of GCase, no increase in enzyme activity was seen. This observation indicates that increases in enzyme activity is due to specific interactions with a protein's known pharmacological chaperone and/or inhibitor.

Example 12

Figure 12:
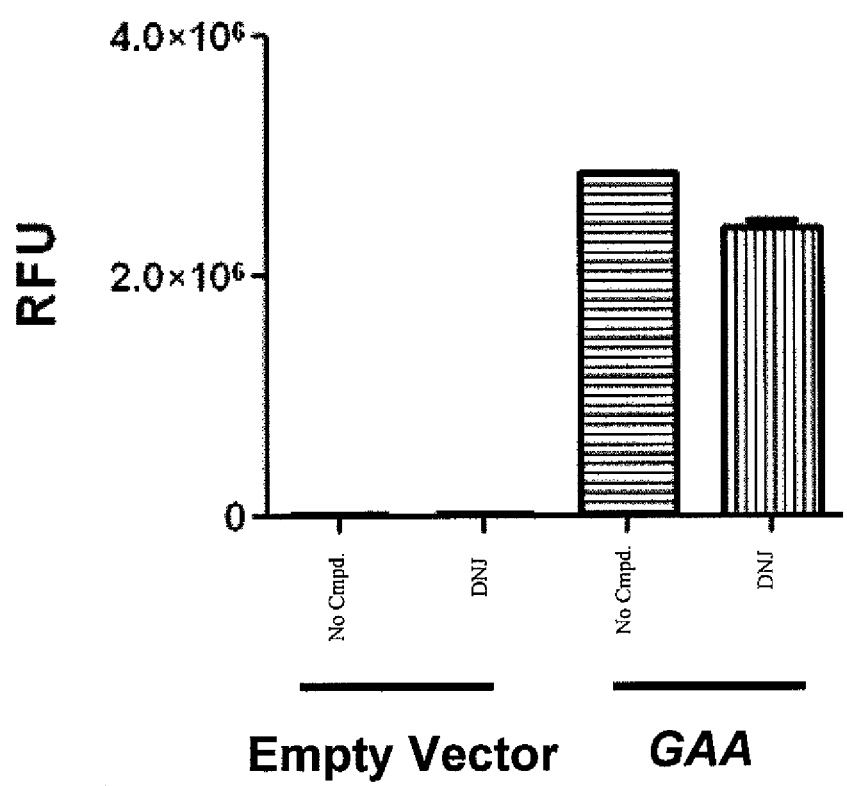

1-Deoxynojirimycin (DNJ) has Little Effect on α-Glucosidase (GAA) Activity from Conditioned Media COS-7 cells were transiently transfected with human GAA plasmid coding for the α-Glucosidase gene (GAA). The various transient transfections were incubated with no pharmacological chaperone or DNJ. After 72-hours of protein expression, the conditioned media from each transfection was harvested, and the level of GAA activity was assessed. As shown in FIG. 12, incubation with DNJ had little effect on the activity of GAA recovered from the media.

Example 13

DGJ Increases α-Gal A (GLA) Activity from Conditioned Media

Figure 13:
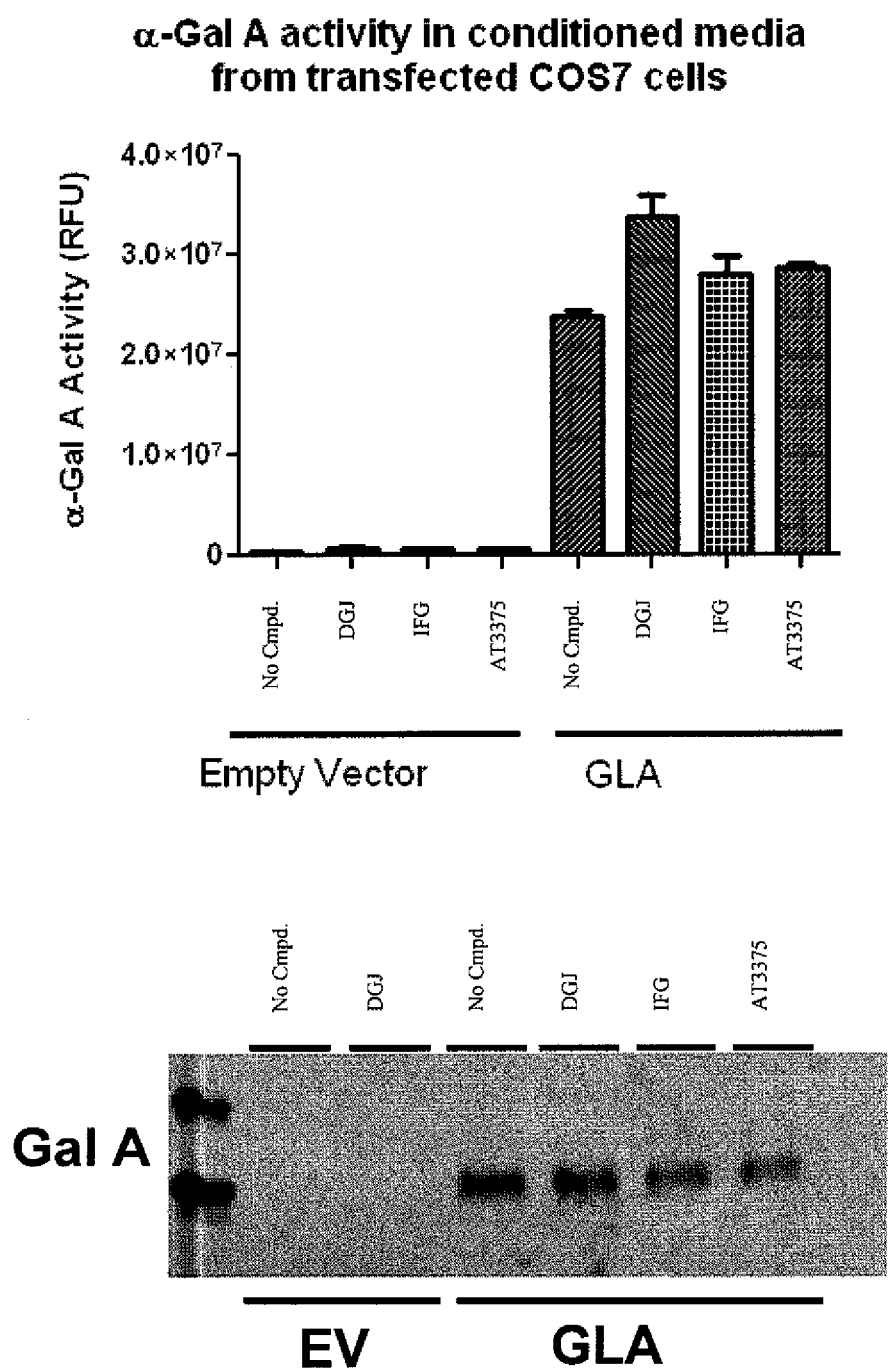

COS-7 cells were transiently transfected with empty vector or a plasmid coding for the α-Gal A gene (GLA). The various transient transfections were incubated with no pharmacological chaperone, DGJ, IFG or AT3375. After 72-hours of protein expression, the conditioned media from each transfection was harvested, and the level of α-Gal A activity was assessed using the substrate 4-MU-β-galactose. As shown in FIG. 13, α-Gal A activity increased slightly when cells were incubated with DGJ and AT3375.

Example 14

Pharmacological Chaperones Stabilize α-Gal A, GAA and GCase

Figure 14:
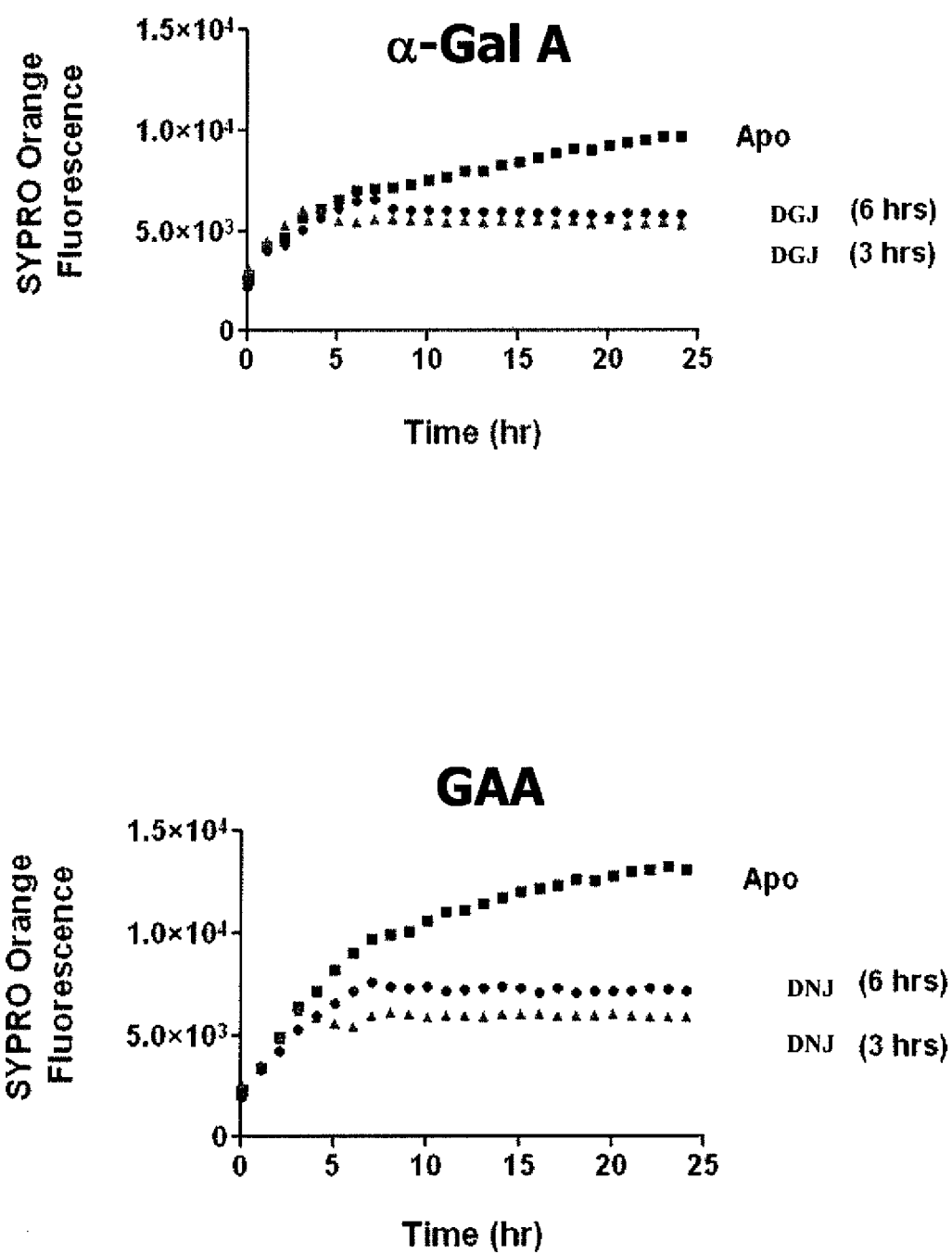
FIG. 14 depicts that addition of 50 μM DGJ or DNJ at 3 or 6 hours after incubation of α-Gal A or GAA in neutral (pH 7.4) buffer at 37° C., respectively, prevents further denaturation of the enzymes as measured by SYPRO dye fluorescence.
Figure 15:
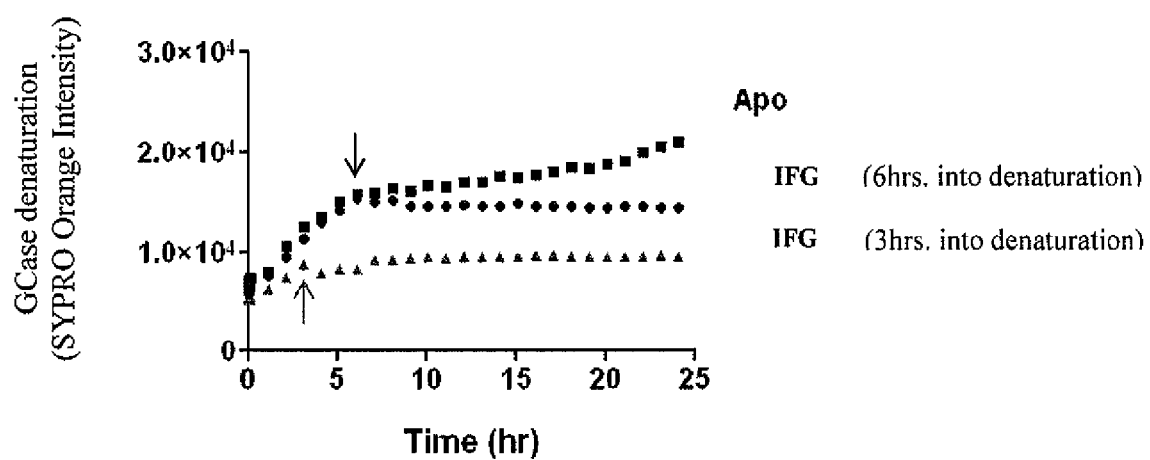
FIG. 15 depicts that addition of 50 μM IFG at 3 or 6 hours after incubation of GCase (Cerezyme®) in neutral (pH 7.4) buffer at 37° C. prevents further denaturation of the enzyme as measured by SYPRO dye fluorescence.

The stability of α-Gal A, α-Glucosidase (GAA), and GCase (Cerezyme®) at 37° C. in neutral (pH 7.4) buffer was measured using the SYPRO Orange for 3, 6 or 24 hours. The effect of DGJ, DNJ or IFG (50 µM) at either 3 or 6 hours on α-Gal A, GAA and GCase denaturation, respectively, was also assessed. As shown in FIG. 14, addition of DGJ or DNJ at either 3 hours or 6 hours prevented further denaturation of α-Gal A and GAA, respectively. FIG. 15 shows that addition of IFG at either 3 hours or 6 hours prevented further denaturation of GCase.

Example 15

IFG Reduces Loss of GCase Activity

Figure 16:
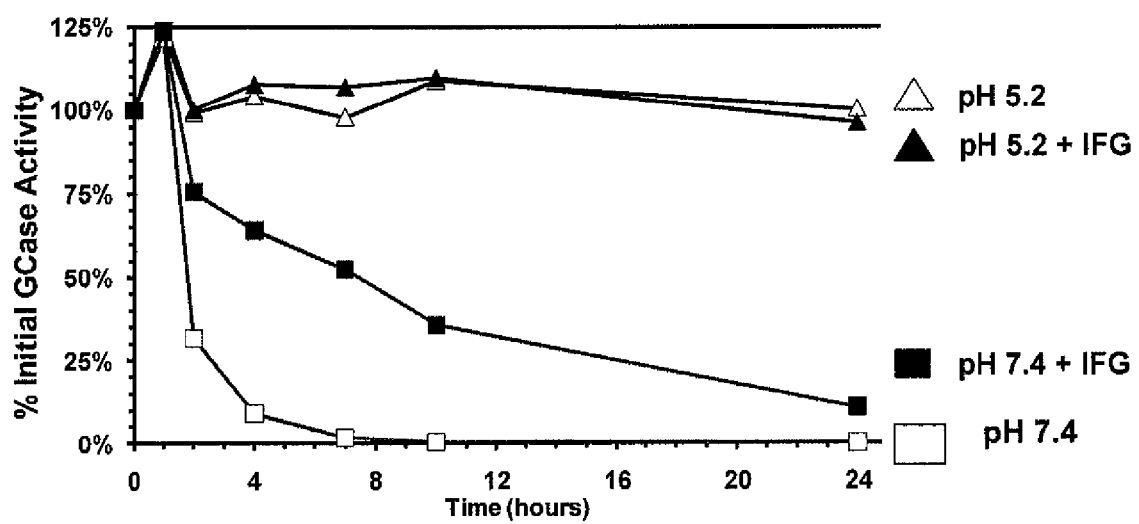
FIG. 16 depicts that of 1 μM IFG significantly increases the stability of GCase (Cerezyme®) at neutral pH (pH 7.4). The activity of GCase (10 nM) at 37° C. in neutral (pH 7.4) or acidic (pH 5.2) buffers±1 μM IFG was assessed as a function of time using 4-MUG.

The activity of GCase (Cerezyme®; 10 nM) at 37° C. in neutral (pH 7.4) or acidic (pH 5.2) buffers±1 µM IFG was assessed as a function of time using 4-MUG. As shown in FIG. 16, IFG significantly increases the stability of GCase at neutral pH.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, product descriptions, GenBank Accession Numbers, and protocols are cited throughout this application, the disclosures of which are incorporated herein by reference in their entireties for all purpose.

What is claimed is:

1. A method for improving the yield of an active recombinant human wild-type acid β-Glucosidase protein expressed by a host cell, wherein the host cell is in media having a pH greater than 5.0, which method comprises
   contacting the host cell in vitro with isofagomine, wherein contacting the host cell with isofagomine increases activity of the acid β-Glucosidase secreted out of the cell, and
   purifying the secreted acid β-Glucosidase from the media, wherein the isofagomine is contacted to the host cell in an amount effective to increase the yield stability of the active acid β-Glucosidase during purification,
   wherein the isofagomine is present at a concentration of at least 3 µM.

2. The method of claim 1, wherein the host cell is a mammalian cell.

3. The method of claim 1, wherein the host cell is selected from the group consisting of CHO cells, HeLa cells, HEK-293 cells, 293T cells, COS cells, COS-7 cells, mouse primary myoblasts, and NIH 3T3 cells.

4. The method of claim 1, wherein contacting the host cell with isofagomine increases the stability of the acid β-Glucosidase in the host cell media.

5. The method of claim 1, further comprising storing the purified acid β-Glucosidase, wherein the isofagomine increases the stability of the acid β-Glucosidase during storage, and wherein the stability of the acid β-Glucosidase is greater than the stability of a recombinant human wild-type acid β-Glucosidase that is not contacted with isofagomine.

6. The method of claim 1, wherein the secreted acid β-Glucosidase is purified to be at least 95% pure.

7. The method of claim 1, wherein purifying the secreted acid β-Glucosidase comprises ammonium sulfate precipitation, column chromatography containing a hydrophobic interaction resin, contacting the secreted acid β-Glucosidase with a cation exchange resin, contacting the secreted acid β-Glucosidase with an anion exchange resin, or contacting the secreted acid β-Glucosidase with a chromatofocusing resin.

* * * * *